(12) United States Patent
Haran et al.

(10) Patent No.: US 9,289,530 B2
(45) Date of Patent: Mar. 22, 2016

(54) SINGLE SCENT ENGINE ARRANGED TO PRODUCE A VARIABLE SCENT OUTPUT

(75) Inventors: Yossi Haran, Modi'in-Maccabim-Reut (IL); Tsafrir Sasson, Kibutz Maagan Michael (IL); Joseph Slupsky, Ramat Hasharon (IL)

(73) Assignee: SCENTCOM, LTD., Kibbutz Lehavot (IL)

( * ) Notice: Subject to any disclaimer, the term of this patent is extended or adjusted under 35 U.S.C. 154(b) by 258 days.

(21) Appl. No.: 13/981,783

(22) PCT Filed: Jan. 26, 2012

(86) PCT No.: PCT/IL2012/050035
§ 371 (c)(1),
(2), (4) Date: Aug. 28, 2013

(87) PCT Pub. No.: WO2012/101647
PCT Pub. Date: Aug. 2, 2012

(65) Prior Publication Data
US 2013/0334337 A1    Dec. 19, 2013

Related U.S. Application Data

(63) Continuation-in-part of application No. 13/143,202, filed as application No. PCT/IL2010/000016 on Jan. 7, 2010, now Pat. No. 8,727,234.

(60) Provisional application No. 61/436,197, filed on Jan. 26, 2011, provisional application No. 61/143,283, filed on Jan. 8, 2009.

(51) Int. Cl.
*B05B 17/06* (2006.01)
*A61L 9/14* (2006.01)
*B05B 17/00* (2006.01)

(52) U.S. Cl.
CPC .............. *A61L 9/14* (2013.01); *B05B 17/0646* (2013.01); *B05B 17/0684* (2013.01); *A61L 2209/11* (2013.01); *A61L 2209/132* (2013.01); *A61L 2209/133* (2013.01)

(58) Field of Classification Search
CPC . A61L 9/14; A61L 2209/11; A61L 2209/132; A61L 2209/133; B05B 17/0646; B05B 17/0684
USPC .............. 239/34, 57, 102.1, 102.2, 302, 303, 239/304, 305
See application file for complete search history.

(56) References Cited

U.S. PATENT DOCUMENTS

| 4,695,434 A | 9/1987 | Spector |
| 4,850,534 A | 7/1989 | Takahashi et al. |

(Continued)

FOREIGN PATENT DOCUMENTS

| EP | 1329228 A1 | 7/2003 |
| EP | 1543844 A2 | 6/2005 |

(Continued)

OTHER PUBLICATIONS

International Search Report for PCT/IL2012/050035 mailed Sep. 7, 2012 by European Patent Office.

(Continued)

*Primary Examiner* — Justin Jonaitis
(74) *Attorney, Agent, or Firm* — Chanoch Kahn; Simon Kahn

(57) ABSTRACT

A scent producing apparatus, the apparatus constituted of: a single atomizer; a control circuitry; and a plurality of scent reservoirs each with a respective controllable release mechanism arranged to release a controlled quantity of the contents of the scent reservoir to the atomizer responsive to the control circuitry. Optionally, at least one solvent reservoir with a respective controllable release mechanism is further provided and arranged to release a controlled quantity of the contents of the at least one solvent reservoir to the single atomizer responsive to the control circuitry. Optionally, a neutralizing agent is provided thus enabling scent production with a predetermined persistence.

20 Claims, 23 Drawing Sheets

(56) References Cited

U.S. PATENT DOCUMENTS

| | | |
|---|---|---|
| 5,435,282 A | 7/1995 | Haber et al. |
| 5,972,290 A | 10/1999 | De Sousa |
| 6,024,783 A | 2/2000 | Budman |
| 6,136,277 A | 10/2000 | Nardini |
| 6,149,873 A | 11/2000 | Potter et al. |
| 6,152,829 A | 11/2000 | Jaidka |
| 6,325,475 B1 | 12/2001 | Hayes et al. |
| 6,530,370 B1 | 3/2003 | Heinonen |
| 6,536,746 B2 | 3/2003 | Watkins |
| 6,539,937 B1 | 4/2003 | Haveri |
| 6,581,915 B2 | 6/2003 | Bartsch et al. |
| 6,592,104 B2 | 7/2003 | Cox |
| 6,602,475 B1 | 8/2003 | Chiao |
| 6,656,041 B1 | 12/2003 | Kaminkow |
| 6,962,151 B1 | 11/2005 | Knoch et al. |
| 7,040,548 B2 | 5/2006 | Rodgers |
| 7,160,515 B2 | 1/2007 | Murdell et al. |
| 7,223,361 B2 | 5/2007 | Kvietok et al. |
| 7,437,061 B2 | 10/2008 | Manne |
| 8,469,293 B2 * | 6/2013 | Doty et al. .................... 239/448 |
| 2003/0107139 A1 | 6/2003 | Wohrle |
| 2003/0206834 A1 | 11/2003 | Chiao et al. |
| 2004/0164101 A1 | 8/2004 | Cornet et al. |
| 2006/0011739 A1 * | 1/2006 | Jaworski ............... A01M 1/205 239/102.2 |
| 2006/0289673 A1 | 12/2006 | Wang et al. |
| 2007/0189919 A1 | 8/2007 | Prince et al. |
| 2007/0258849 A1 | 11/2007 | Kent |
| 2008/0043204 A1 | 2/2008 | Guo |
| 2008/0191370 A1 | 8/2008 | Pankhurst et al. |
| 2011/0266359 A1 * | 11/2011 | Haran ............................. 239/6 |

FOREIGN PATENT DOCUMENTS

| | | |
|---|---|---|
| WO | 0012143 | 3/2000 |
| WO | 00/53301 A1 | 9/2000 |
| WO | 0232470 A1 | 4/2002 |
| WO | 03028775 A1 | 4/2003 |
| WO | 03059403 A1 | 7/2003 |
| WO | 2004/043502 A1 | 5/2004 |
| WO | 2004105878 A1 | 12/2004 |
| WO | 2005092400 A1 | 10/2005 |
| WO | 2006058125 A2 | 6/2006 |
| WO | 2006074562 A1 | 7/2006 |
| WO | 2010079485 A1 | 7/2010 |

OTHER PUBLICATIONS

Written Opinion of the International Searching Authority for PCT/IL2012/050035 mailed Sep. 7, 2012 by European Patent Office.

* cited by examiner

SINGLE SCENT ENGINE ARRANGED TO PRODUCE A VARIABLE SCENT OUTPUT

CROSS-REFERENCE TO RELATED APPLICATIONS

This application is a National Phase application of PCT/IL2012/050035 with International Filing Date Jan. 26, 2012, and which PCT/IL2012/050025 claims priority from U.S. Provisional Application 61/436,197 filed Jan. 26, 2011. Additionally, this application is a continuation-in-part of U.S. patent application Ser. No. 13/143,202 which is a National Phase application of PCT/IL2010/000016 with International Filing Date Jan. 7, 2010, and which PCT/IL2010/000016 claims priority from U.S. Provisional Application 61,143,283 filed Jan. 8, 2009.

TECHNICAL FIELD

The invention relates generally to the field of electronically controlled scent production, and more particularly to an apparatus with an electronically controlled atomizer arranged to produce a plurality of scents.

BACKGROUND

Video games, particularly computer based games and game stations, have become extremely popular. The combination of visual and audio stimulation has succeeded in capturing a significant portion of people's leisure time. Various games have been developed, with associated hardware, that further involves the sense of touch, by allowing for varying input instruments. In one example, a musical instrument such as a mock guitar, is utilized as a game input, thus involving the sense of touch.

Games have been developed providing for a virtual reality world, again based on stimulating various user senses. However, to date, the remaining senses, namely smell and taste have not been stimulated.

While the above has been described in relation to games, this is not meant to be limiting in any way. Many other uses of an electronically controlled scent system exist, such as alarms or for the improvement of communication, are specifically included herein.

U.S. Patent Application Publication S/N 2008/0043204 published Feb. 21, 2008 to Guo, is addressed to a digital scent movie projector with sound channels. Scent making devices release a scent into a cinema, thereby providing for film arts to provide a sense of sight, hearing and smell as part of movie.

A movie proceeds along a predetermined script, which does not allow for user interaction. Thus, the scents to be provided by Guo are predetermined, and are not subject to change by a user action. Additionally, scent provided by Guo is arranged for releasing scent into a large space, which is not appropriate for an individual use. Furthermore, the scent of Guo utilizes a plurality of scent cans feeding pressure reducing valves, and is thus limited in terms of its ability to accurately control the amount of persistence of the scent. Furthermore, a plurality of scent producers are required, thus adding to cost.

An additional problem with many prior art solutions is residual scent; particularly the scent continues to linger for a relatively long period after the desired emission, know as scent persistence. Residual scent is particularly problematic in the case of individual scent needs, such as computer gamers, which often play in undisturbed spaces, where scents easily linger. In particular, any physical element which has been contacted by a concentration of scent molecules continues to exude the scent. The residual scent further contaminates additional scents, and thus the need for a scent producing element for which persistence is controlled is readily apparent.

World Intellectual Property Organization publication WO 2010/079485 A1 published 15 Jul. 2010 to Scentcom, Ltd., the entire contents of which is incorporated herein by reference, is addressed to an electronically controlled scent producing element. Unfortunately, the electronically controlled scent producing element is arranged for use with a single container comprising a volatile scent liquid. To alternately produce one of a plurality of scents, a combination of electronically controlled scent producing elements are preferably supplied, as described in World Intellectual Property Organization Publication WO 2010/079486 A1 published 15 Jul. 2010 to Scentcom, Ltd., the entire contents of which is incorporated herein by reference, which is addressed to a method and apparatus for computer controlled scent delivery. Disadvantageously, the apparatus described is of a large size, requiring a central air mover.

Prior art devices arranged to deliver one of a plurality of scents thus typically require an atomizer associated with each of the plurality of scents. Such a plurality of atomizers prevents miniaturization.

Additionally, and without limitation, a device arranged to produce a plurality of scents which may be called on to produce those scents responsive to a game console, or other device, may not release the various scents at an equal rate. Volatile scent liquid is typically comprised of a mixture of fragrance and a solvent, also known as a diluting agent, which occupies volume. A requirement to provide any of the plurality of scents up to a predetermined number of emissions for any of the scents, thus requires that each scent occupy sufficient volume to meet the requirement. The total volume of the device is thus the volume of the minimum required number of emissions times the number of scent types, thus further preventing miniaturization.

SUMMARY

Accordingly, it is a principal object of the present invention to overcome at least some of the disadvantages of prior art. This is accomplished in certain embodiments by providing a control circuitry and a single atomizer, the single atomizer in communication with a plurality of scent reservoirs, each loaded with a particular volatile scent liquid. Each of the plurality of scent reservoirs are arranged to controllably release their contents to the single atomizer. In one particular embodiment the single atomizer is composed of a plurality of micro-needles in communication with a plate and in communication with each of a translation mechanism and a vibration mechanism. The translation mechanism and vibration mechanism are operative responsive to the control circuitry to alternately atomize one or more volatile scent liquids received from the scent reservoirs, and provide ultrasonic cleaning to the single atomizer to remove any residual scent between atomizations. Any blending of scents is thus provided by releasing a plurality of volatile scent liquids from the various scent reservoirs, with blending performed by the single atomizer.

In one further embodiment, at least one solvent reservoir is further provided in combination with the single atomizer, and the plurality of scent reservoirs are each arranged to be loaded with a super-concentrated volatile scent liquid.

In one further embodiment the single atomizer is composed of a plurality of segments, wherein each of the plurality of segments is in communication with a particular one of the plurality of scent reservoirs. In an embodiment in which the solvent reservoir is provided, preferably, each of the segments is further in communication with one of the solvent reservoirs. Blending of scents is performed by releasing a controlled quantity of volatile scent liquid, optionally as a controlled quantity of super-concentrated volatile scent liquid, from a plurality of scent reservoirs to their respective segments, with blending performed on the atomized scents after exiting the respective segments of the single atomizer.

In one independent embodiment, a scent producing apparatus is provided, the apparatus comprising: a single atomizer; a control circuitry; and a plurality of scent reservoirs each with a respective controllable release mechanism, the respective controllable release mechanism arranged to release a controlled quantity of the contents of the scent reservoir to the single atomizer responsive to the control circuitry.

In one embodiment, the scent producing apparatus further comprises at least one solvent reservoir with a respective controllable release mechanism, each of the respective solvent reservoir controllable release mechanism arranged to release a controlled quantity of the contents of the at least one solvent reservoir to the single atomizer responsive to the control circuitry, wherein the plurality of scent reservoirs are radially arrayed about a common center axis comprising an extension of the at least one solvent reservoir.

In another embodiment, each of the scent reservoirs comprises a port towards the single atomizer and each of the respective scent reservoir controllable release mechanisms comprises a piezoelectric element in communication with the port, the piezoelectric element coupled to an output of the control circuitry and responsive to a first signal state at the output of the control circuitry to release a predetermined quantity of the contents of the scent reservoir through the port to the single atomizer, and to a second signal state to cease the release of the controlled quantity of the contents of the scent reservoir through the port to the single atomizer. In one further embodiment, the first signal state exhibits a plurality of sub-states, each of the plurality of sub-states arranged to enable the piezoelectric element of the respective scent reservoir controllable release mechanism to release through the port a different predetermined quantity of the contents of the scent reservoir.

In one embodiment, the scent producing apparatus further comprises at least one solvent reservoir with a respective controllable release mechanism, the solvent reservoir controllable release mechanism arranged to release a controlled quantity of the contents of the at least one solvent reservoir to the single atomizer responsive to the control circuitry, wherein the at least one solvent reservoir comprises a port towards the single atomizer and wherein the respective solvent reservoir controllable release mechanism comprises a piezoelectric element in communication with the port, the piezoelectric element of the respective solvent reservoir controllable release mechanism coupled to an output of the control circuitry and responsive to a first signal state at the output of the control circuitry to release a predetermined quantity of the contents of the at least one solvent reservoir through the port to the single atomizer, and to a second signal state to cease the release of the controlled quantity of the contents of the at least one solvent reservoir through the port to the single atomizer. In one further embodiment, the first signal state exhibits a plurality of sub-states, each of the plurality of sub-states arranged to enable the piezoelectric element of the solvent reservoir to release through the port a different predetermined quantity of the contents of the solvent reservoir.

In another embodiment, the single atomizer comprises a plurality of segments, each of the scent reservoirs associated with, and arranged to release the controlled quantity to a particular one of the plurality of segments. In one further embodiment, the control circuitry is arranged to enable each of at least two of the plurality of scent release mechanisms to release a controlled quantity of the contents of the respective scent reservoir to the respective atomizer segment so as to produce a compound scent. In another further embodiment, the scent producing apparatus further comprises a plurality of solvent reservoirs each with a respective controllable release mechanism arranged to release a controlled quantity of the contents of the respective solvent reservoir to a respective one of the plurality of segments of the single atomizer responsive to the control circuitry, wherein the control circuitry is arranged to enable at least two of the scent reservoir controllable release mechanisms and at least two of the solvent reservoir controllable release mechanisms to release a controlled quantity of the contents of the respective scent reservoirs and solvent reservoirs to the single atomizer so as to produce a compound scent.

In one embodiment, the single atomizer comprises: a plate exhibiting a plurality of perforations extending from a first face of the plate to a second face of the plate opposing the first face; a plurality of micro-needles in communication with the plate, each of the plurality of micro-needles extending longitudinally from a base end to a tip end, and arranged to mate with one of the plurality of perforations; and at least one of: a translation mechanism in communication with one of the plate and the plurality of micro-needles and responsive to the control circuitry, the translation mechanism arranged to translate the plurality of micro-needles in relation to the plate from a first position wherein each of the plurality of micro-needles is seated within a respective one of the plurality of the perforations to a second position wherein each of the plurality of micro-needles is at least partially removed from a wall of the respective one of the plurality of perforations; and a vibrator in communication with at least one of the plate and the plurality of micro-needles.

In another embodiment, the single atomizer comprises a plate exhibiting a plurality of release ports extending from a first face of the plate to a second face of the plate opposing the first face and a vibrator in communication with the plate and responsive to the control circuitry, and wherein each of the plurality of controllable release mechanisms comprises: a local portion of a respective one of the plurality of scent reservoirs; a micro-needle, in communication with the plate of the atomizer and extending longitudinally from a base end to a tip end, the micro-needle arranged to mate with one of the plurality of release ports; and a translation mechanism in communication with the micro-needle and responsive to the control circuitry, wherein the control circuitry is arranged to: translate, via the translation mechanism, the micro-needle in relation to the plate from a first position, wherein the micro-needle is seated within the respective release port, to a second position wherein the micro-needle is at least partially removed from a wall of the respective release port; and vibrate the plate to thereby atomize the released controlled quantity of the contents of the respective scent reservoir, wherein the release of a controlled quantity of the contents of the respective scent reservoir is responsive to the micro-needle being in the second position.

In one embodiment, each of the plurality of scent reservoirs comprises a scented material. In another embodiment, the arrangement to release a controlled quantity of the contents of the scent reservoir comprises spraying a controlled quantity of the contents of the scent reservoir into the single atomizer.

In one independent embodiment, a method of scent production is provided, the method comprising: providing a single atomizer; providing a plurality of scent reservoirs, each arranged to comprise a volatile scent liquid; and releasing a controlled quantity of volatile scent liquid from at least one of the provided plurality of scent reservoirs to the provided single atomizer to thereby produce a scent.

In one embodiment, the provided single atomizer comprises a plurality of segments each associated with a particular one of the provided plurality of scent reservoirs, and wherein the releasing a controlled quantity of volatile scent liquid from at least one of the provided plurality of scent reservoirs to the provided single atomizer comprises releasing a controlled quantity of volatile scent liquid from at least one of the provided plurality of scent reservoirs to the associated segment of the provided single atomizer. In one further embodiment, the releasing a controlled quantity of volatile scent liquid from at least one of the provided plurality of scent reservoirs to the provided single atomizer comprises releasing a controlled quantity of volatile scent liquid from each of a plurality of the provided plurality of scent reservoirs to the associated atomizer segment of the provided single atomizer thereby producing a compound scent.

In another embodiment, the releasing a controlled quantity of volatile scent liquid from at least one of the provided plurality of scent reservoirs to the provided single atomizer comprises releasing a controlled quantity of volatile scent liquid from each of a plurality of the provided plurality of scent reservoirs to the provided single atomizer thereby producing a compound scent.

In one embodiment, the provided single atomizer comprises a plate and a plurality of micro-needles, and wherein the method further comprises, after producing the scent, ultrasonically cleaning a face of the plate and tip ends of the plurality of micro-needles. In another embodiment, the volatile scent liquid of each of the plurality of scent reservoirs is a super-concentrated volatile scent liquid, the method further comprising: providing at least one solvent reservoir comprising a common solvent for the super-concentrated volatile scent liquids; and releasing a controlled quantity of common solvent from the provided at least one solvent reservoir to the provided atomizer.

In one embodiment, the provided single atomizer comprises a plate exhibiting a plurality of release ports extending from a first face of the plate to a second face of the plate opposing the first face, the method further comprising: providing a plurality of controllable release mechanisms, each of the provided plurality of controllable release mechanisms in communication with one of the provided plurality of scent reservoirs and comprising a micro-needle, in communication with the plate of the provided single atomizer and extending longitudinally from a base end to a tip end, the micro-needle arranged to mate with one of the plurality of release ports; translating the micro-needle of one of the plurality of controllable release mechanisms in relation to the plate from a first position, wherein the micro-needle is seated within the respective release port, to a second position wherein the micro-needle is at least partially removed from a wall of the respective release port; and atomizing, in the provided atomizer, the released controlled quantity of volatile scent liquid, wherein the releasing a controlled quantity of volatile scent liquid is responsive to the micro-needle of the respective controllable release mechanism being in the second position. In another embodiment, each of the plurality of scent reservoirs comprises a scented material.

In one embodiment, the method further comprises: releasing a pre-determined quantity of neutralizing agent to the atomizer; atomizing, in the provided atomizer, the released pre-determined quantity of volatile scent liquid and the released pre-determined quantity of neutralizing agent to provide the scent. In another embodiment, the releasing a controlled quantity of volatile scent liquid comprises spraying a controlled quantity of volatile scent liquid into the provided single atomizer.

Additional features and advantages of the invention will become apparent from the following drawings and description.

BRIEF DESCRIPTION OF THE DRAWINGS

For a better understanding of various embodiments of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION

Figure 1A:
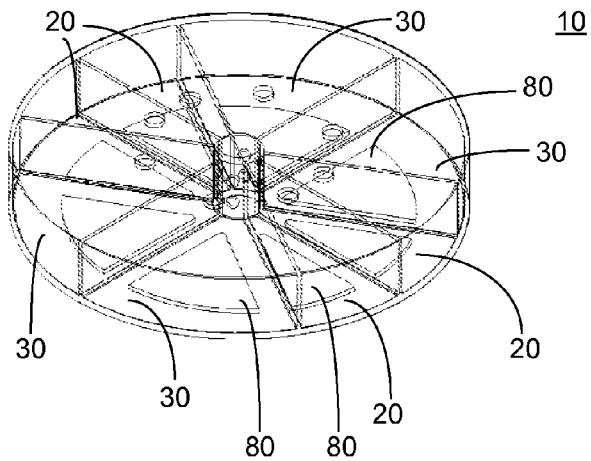
FIGS. 1A-1D illustrate a plurality of views of an exemplary embodiment of a multi-scent cartridge comprising a plurality of scent reservoirs and a plurality of solvent reservoirs.

Before explaining at least one embodiment in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The term atomizer, as used herein, is meant to include any apparatus arranged to nearly instantly convert a liquid into a fine mist, and is synonymous with the term nebulizer, with the difference that the term nebulizer it typically used to indicate that the apparatus is slow to atomize, and exhibits less control over the amount of fine mist created responsive to a command.

Figure 1B:
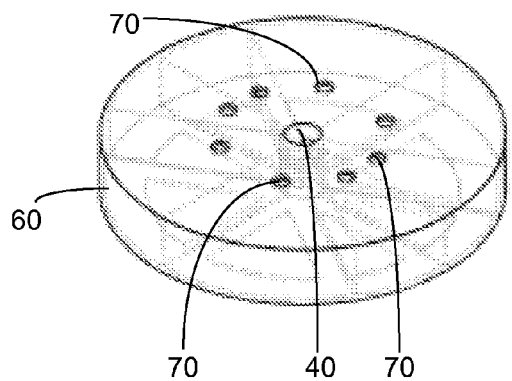
Figure 1C:
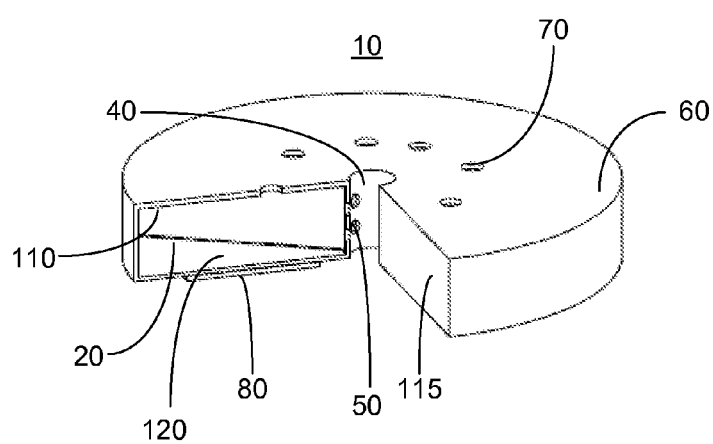
Figure 1D:
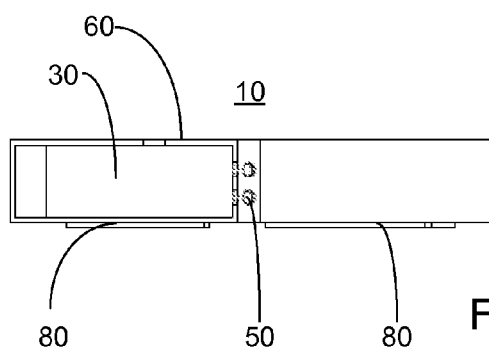
Figure 1E:
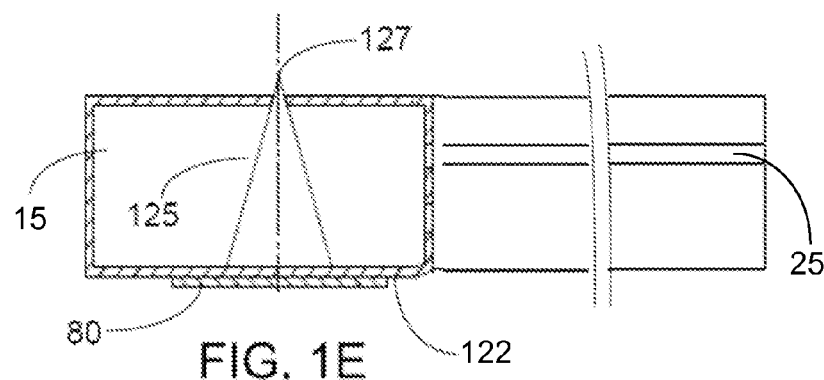
FIGS. 1E-1G illustrate an embodiment of a first embodiment of the operation of the multi-scent cartridge of FIGS. 1A-1D.
Figure 1F:
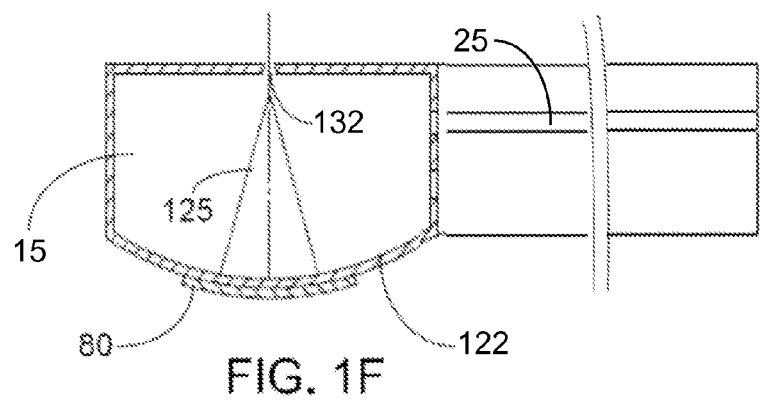
Figure 1G:
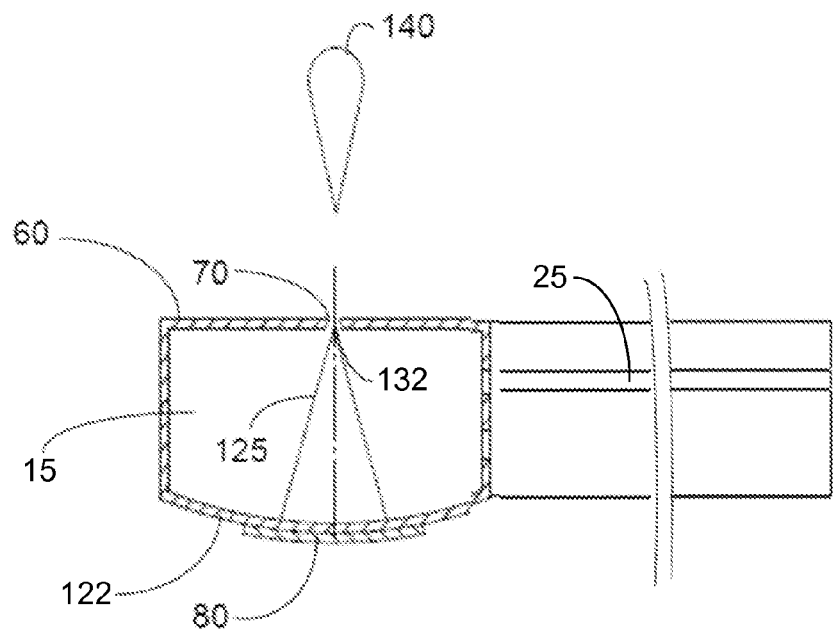
Figure 1H:
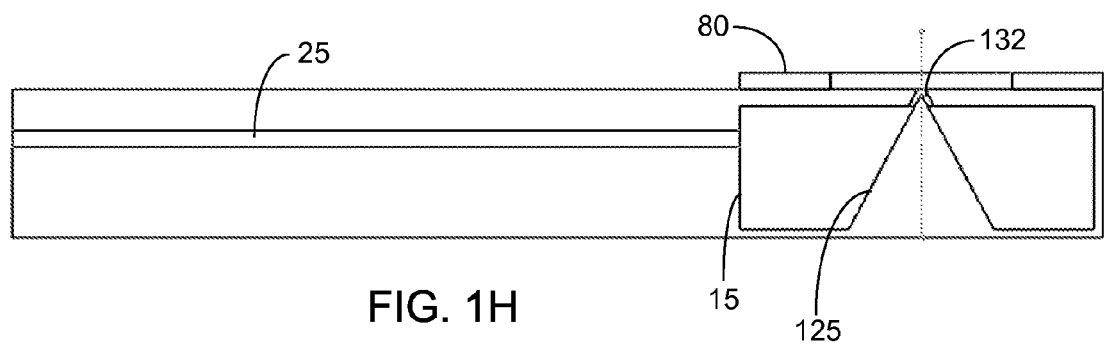
FIGS. 1H-1J illustrate an embodiment of a second embodiment of the operation of the multi-scent cartridge of FIGS. 1A-1D.
Figure 1I:
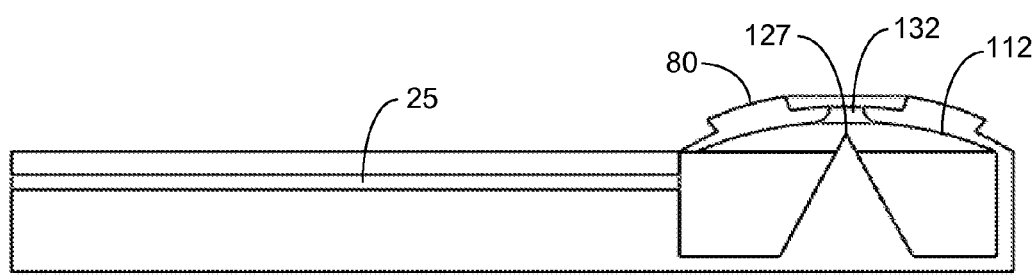
Figure 1J:
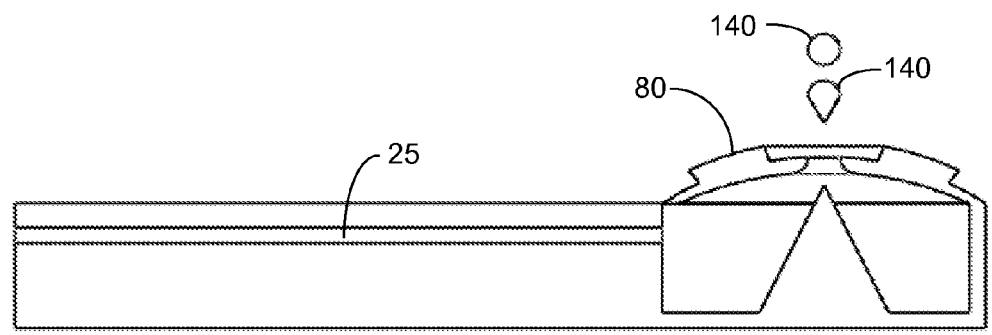

FIGS. 1A-1D illustrate a plurality of exploded views of an exemplary embodiment of a multi-scent cartridge 10, and FIGS. 1E-1G illustrate a first embodiment of the operation of multi-scent cartridge 10, the figures being taken together; and FIGS. 1H-1J illustrate a second embodiment of the operation of multi-scent cartridge 10. FIG. 1A illustrates a perspective transparent view of multi-scent cartridge 10; FIG. 1B illustrates a perspective, partially transparent view of multi-scent cartridge 10; FIG. 1C illustrates a partially cut view of multi-scent cartridge 10; FIG. 1D illustrates a side cut view of multi-scent cartridge 10; FIG. 1E illustrates a first embodiment of the operation of multi-scent cartridge 10 in a first position; FIG. 1F illustrates the first embodiment of the operation of multi-scent cartridge 10 in a second position; FIG. 1G illustrates the first embodiment of the operation of multi-scent cartridge 10 in a third position; FIG. 1H illustrates a second embodiment of the operation of multi-scent cartridge 10 in a first position; FIG. 1I illustrates the second embodiment of the operation of multi-scent cartridge 10 in a second position; FIG. 1J illustrates the second embodiment of the operation of multi-scent cartridge 10 in a third position.

Multi-scent cartridge 10 comprises: a plurality of scent reservoirs 20, each comprising a super-concentrated volatile scent liquid; a plurality of solvent reservoirs 30, each comprising a common solvent; and an outer shell 60, exhibiting a plurality of ports 70. Further illustrated is a solvent reservoir extension 40, exhibiting a plurality of holes 50, each hole 50 being a hole in a wall of a particular solvent reservoir 30. Additionally illustrated is a plurality of controllable release mechanisms 80, each in communication with a particular one of the plurality of scent reservoirs 20 and the plurality of solvent reservoirs 30. Each of the plurality of scent reservoirs 20 and the plurality of solvent reservoirs 30 exhibits a first wall 110 and a second wall 120 opposing first wall 110. First wall 110 exhibits at least one aperture 130 constituted of a particular port 70 of outer shell 60. In one embodiment, first wall 110 is constituted of a compliant material. Second wall 120 is in one embodiment constituted of a compliant material.

In one embodiment, each scent reservoir 20 has associated therewith a scent drop on demand unit 15, such that the respective controllable release mechanism 80 is in communication with scent drop on demand unit 15. As described in relation to scent reservoir 20, scent drop on demand unit 15 exhibits a first wall 112 and a second wall 122 opposing first wall 112. First wall 112 exhibits at least one aperture 132 constituted of a particular port 70. In one embodiment, the distance between first wall 112 and second wall 122 is 100-300 microns. Each scent drop on demand unit 15 is connected to the respective scent reservoir 20 via a feeder channel 25, as will be described below in relation to FIG. 2G.

In one embodiment, second wall 122 of scent release drop on demand unit 15 has connected thereto at least one optional micro-needle 125 extending longitudinally from second wall 120 to a tip end 127 and opposing a respective aperture 132. Each optional micro-needle 125 forms the needle section of a particular micro-valve and the respective aperture 132 forms the chassis section of the respective micro-valve, the plurality of micro-valves forming a micro-valve array. In one embodiment the diameter of each optional micro-needle 125 at second wall 122 is 25-30 microns and in one further embodiment is about 30 microns.

Each of the plurality of optional micro-needles 125 is arranged to mate with a respective aperture 132. Preferably, a portion of each optional micro-needle 125, and particularly the portion extending through the respective aperture 132 is conically shaped with an apex extending away from second wall 122. Apertures 132 are preferably similarly conically shaped, such that when the respective optional micro-needles 125 are in the first position, as will be described below, each of the respective optional micro-needles 125 is seated against the inner walls of the respective aperture 132 sufficiently to seal aperture 132 against any volatile liquid flow there through. In one embodiment each of the respective optional micro-needles 125 is seated flush against the inner walls of the respective aperture 132 thus sealing aperture 132 against any volatile liquid flow there through.

In one embodiment (not shown), each solvent reservoir 30 is replaced with a solvent drop on demand unit. The solvent drop on demand unit is in all respects similar to scent drop on demand unit 15, with the exception that the solvent drop on demand unit exhibits at least one hole 50 as described above in relation to solvent reservoir 30.

In one embodiment, each of the plurality of scent reservoirs 20 and the plurality of solvent reservoirs 30 is generally triangularly shaped. In one embodiment, as illustrated in FIGS. 1A-1G, controllable release mechanisms 80 are triangular shaped. In another embodiment (not shown), controllable release mechanisms 80 are ring shaped. In one embodiment, the plurality of scent reservoirs 20 and the plurality of solvent reservoirs 30 are radially arranged around solvent reservoir extension 40 and outer shell 60 is generally circular in shape. In one embodiment, a single solvent reservoir 30 is adjacent to each scent reservoir 20. In one embodiment, a pair of scent reservoirs 20 are adjacent to each other, and a pair of solvent reservoirs 30 are adjacent to either side of the pair of scent reservoirs 20. Each of the plurality of scent reservoirs 20 and the plurality of solvent reservoirs 30 exhibits at least one of the plurality of ports 70. In one non-limiting embodiment, each of the plurality of scent reservoirs 20 and the plurality of solvent reservoirs 30 exhibits a particular one of the plurality of ports 70. In one embodiment (not illustrated), each of the plurality of controllable release mechanisms 80 comprises an electrode arranged to provide an electric power to the respective controllable release mechanism 80, the electrode receiving power from a control circuitry.

Solvent reservoir extension 40 is arranged to provide a common solvent to the one or more solvent reservoirs 30, as will be described below in relation to FIG. 2A. The term common solvent is used herein as a solvent used for the contents of each of the scent reservoirs 20, and in one particular embodiment is water. In one embodiment, each super-concentrated volatile scent liquid of a particular scent reservoir 20 exhibits a particular scent different from the scents exhibited by super-concentrated volatile scent liquid of the other scent reservoirs 20.

In one embodiment, each controllable release mechanism 80 comprises a piezoelectric element. In one embodiment, as illustrated in FIGS. 1A-1D, each of the plurality of controllable release mechanisms 80 is in communication with a portion of second wall 120 associated with a respective one of the plurality of scent reservoirs 20 and the plurality of solvent reservoirs 30.

As described above, in one embodiment a plurality of scent drop on demand units 15 and solvent drop on demand units are provided. In one further embodiment, as illustrated in FIGS. 1E-1G, each of the plurality of controllable release mechanisms 80 is in communication with a portion of second wall 122 of the associated scent drop on demand unit 15 or solvent drop on demand unit. In another further embodiment, as illustrated in FIGS. 1H-1J, each of the plurality of controllable release mechanisms 80 is in communication with a portion of first wall 112 of the associated scent drop on demand unit 15 or solvent drop on demand unit. In such an embodiment, each controllable release mechanism 80 exhibits at least one perforation arranged to be aligned with a respective port 70 and to allow the contents of the respective scent drop on demand unit 15 or solvent drop on demand unit to exit therethrough.

Preferably, the diameter of ports 70 are arranged to be small enough such that super-concentrated volatile scent liquid stored in a respective scent reservoir 20 and common solvent stored in a respective solvent reservoir 30 cannot exit through the respective port 70 solely in response to gravity, the diameter of ports 70 being selected responsive to the viscosity of the super-concentrated volatile scent liquid and common solvent. Additionally, in an embodiment where optional micro-needles 125 are not provided in scent drop on demand units 15 and the solvent drop on demand units, the diameter of ports 70 are arranged to be small enough such that super-concentrated volatile scent liquid stored in a respective scent drop on demand unit 15 and common solvent stored in a respective solvent drop on demand unit cannot exit through the respective port 70 solely in response to gravity, the diameter of ports 70 being selected responsive to the viscosity of the super-concentrated volatile scent liquid and common solvent.

In operation, in the embodiment where scent drop on demand units 15 and the solvent drop on demand units are not provided, each controllable release mechanism 80 is arranged to release a controlled amount of volatile scent liquid from a particular associated scent reservoir 20 and a controlled amount of common solvent from a particular associated solvent reservoir 30. In order to release a controlled quantity of volatile scent liquid or common solvent, a low frequency electrical signal is provided to the associated controllable release mechanism 80. At a high state of the low frequency signal, controllable release mechanism 80 expands, thereby expanding the portion of second wall 120 of the respective associated one of the plurality of scent reservoirs 20 or the plurality of solvent reservoirs 30. The expansion of second wall 120 applies sufficient pressure to the super-concentrated volatile scent liquid of the respective scent reservoir 20 or the common solvent of the respective solvent reservoir 30, so as to release a single drop of the super-concentrated volatile scent liquid or the common solvent, respectively, through the respective port 70. In order to cease the release of volatile scent liquid and/or common solvent, the control circuitry is arranged to disconnect the electrical signal from the respective controllable release mechanism 80. Controllable release mechanism 80 fully expands, thereby returning the respective second wall 120 to its original position.

In the embodiment where scent drop on demand units 15 and the solvent drop on demand units are provided, each controllable release mechanism 80 is arranged to release a controlled amount of volatile scent liquid from a particular associated scent drop on demand unit 15 and a controlled amount of common solvent from a particular associated solvent drop on demand unit, as will be described below.

In the embodiment where controllable release mechanisms 80 are each in communication with a particular second wall 122, as illustrated in FIGS. 1E-1G, in a first position wherein controllable release mechanism 80 is not contracted as illustrated in FIG. 1E, each optional micro-needle 125 is seated against the walls of the respective aperture 132 sufficiently to close the respective port 70 against the flow of volatile scent liquid. Optionally micro-needles 125 are seated flush against the walls of the respective aperture 132. In order to release a controlled quantity of volatile scent liquid or common solvent, a low frequency electrical signal and a DC electrical signal are provided to the associated controllable release mechanism 80. At a high state of the low frequency signal, controllable release mechanism 80 is contracted, thereby bending second wall 122 and translating optional micro-needles 125 to a second position as illustrated in FIG. 1F, wherein optional micro-needles 125 are removed from apertures 132. In one embodiment, optional micro-needles 125, in the second position, are only partially removed from apertures 132, however optional micro-needles 125 are removed sufficiently from apertures 132 so as to allow entry of volatile scent liquid or common solvent into the respective apertures 132. The bending of second wall 122 enlarges the particular scent drop on demand unit 15 or solvent drop on demand unit, thereby additional super-concentrated volatile scent liquid enters the particular scent drop on demand unit 15 through the respective feeder channel 25 or additional common solvent enters the particular solvent drop on demand unit through solvent reservoir extension 40.

At a low state of the low frequency signal, controllable release mechanism 80 partially expands as illustrated in FIG. 1G, thereby second wall 122 partially returns to its original state and optional micro-needles 125 are translated to a third position, the third position being between the first position and the second position. Controllable release mechanism 80 remains partially contracted because of the DC electrical signal. As second wall 122 partially returns to its original state, the size of the particular scent drop on demand unit 15 or solvent drop on demand unit shrinks thereby droplets 140 of volatile scent liquid or common solvent are released through the respective port 70, via the associated aperture 132, as will be described below in relation to FIGS. 2A-2G. Thus, droplets 140 of volatile scent liquid and common solvent are released using Drop on Demand technology with the addition of optional micro-needles 125. Advantageously, in the first position optional micro-needles 125 prevent volatile scent liquid and common solvent from being uncontrollably released through ports 70.

In order to cease the release of volatile scent liquid and/or common solvent, the control circuitry is arranged to disconnect the electrical signal from the respective controllable release mechanism 80. Controllable release mechanism 80 fully expands, thereby returning optional micro-needles 125 to the first position.

In the embodiment where optional micro-needles 125 are not provided, controllable release mechanism 80 is arranged to expand so as to release droplets 140 of volatile scent liquid or common solvent, as known to one skilled in the art of Drop on Demand technology. Specifically, the operation is in all respects similar to the operation of scent drop on demand units 15 and solvent drop on demand units as described above, with the exception that a DC electrical signal is not provided.

In the embodiment where controllable release mechanisms 80 are each in communication with particular first wall 112, the operation of controllable release mechanisms 80 is as described above with the exception that optional micro-needles 125 remain in a fixed position and the respective first wall 112 is translated, as described above in relation to the translation of second wall 122.

Figure 2A:
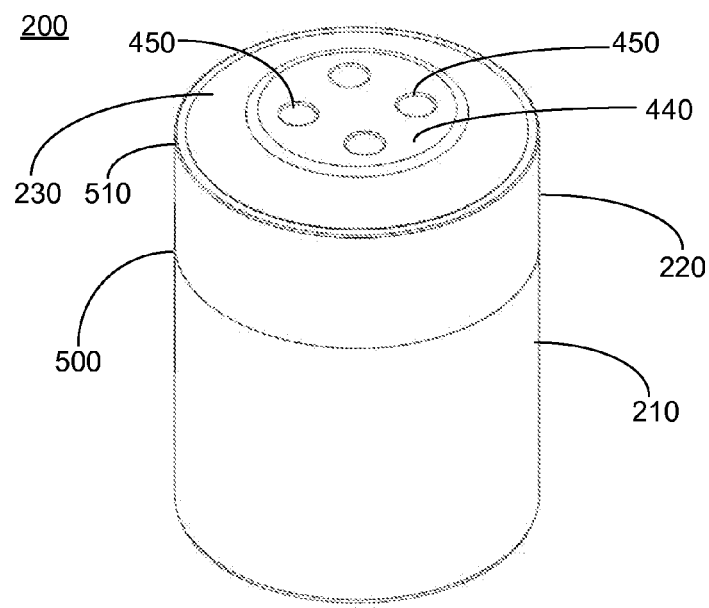
FIGS. 2A-2G illustrate a plurality of exploded views of an exemplary embodiment of a scent producing apparatus, comprising a segmented atomizer, a segmented nozzle device, an extended solvent reservoir and the multi-scent cartridge of FIGS. 1A-1E, each of the segments in communication with a particular one of the scent reservoirs.
Figure 2B:
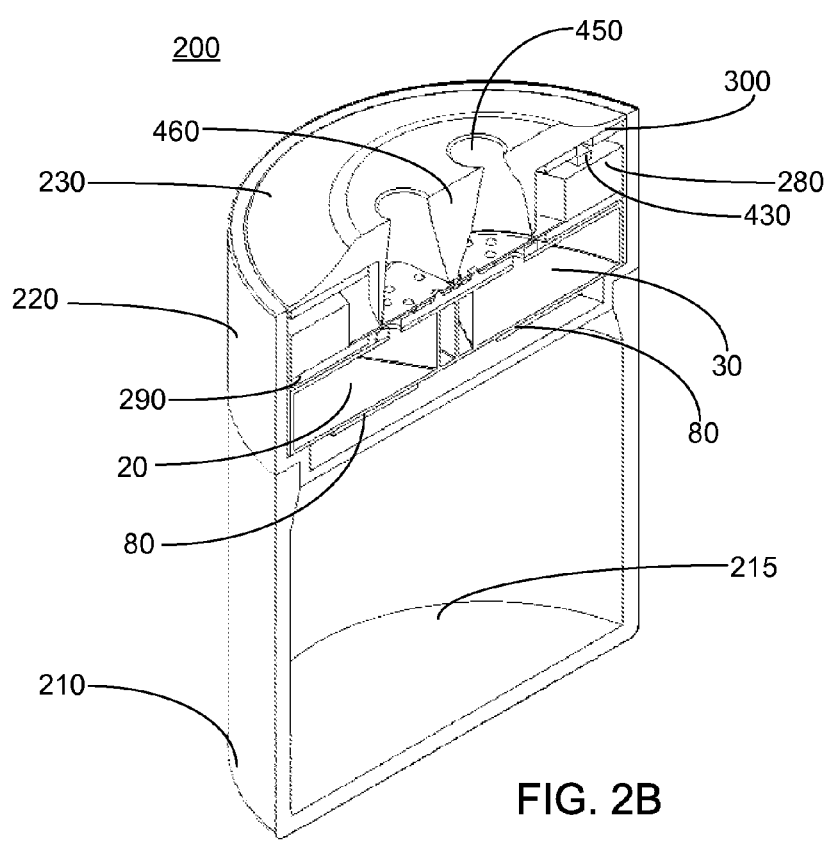
Figure 2C:
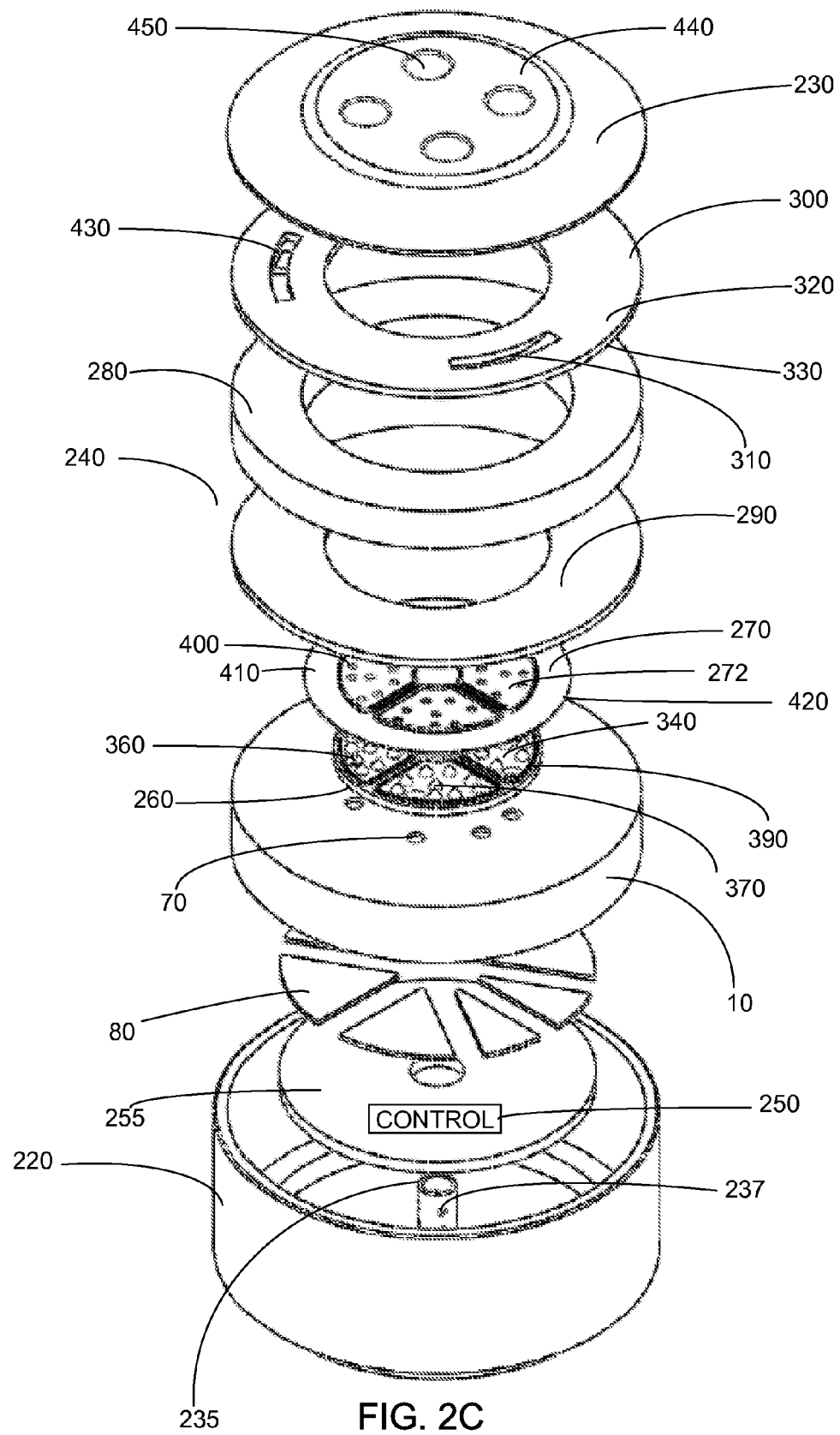
Figure 2D:
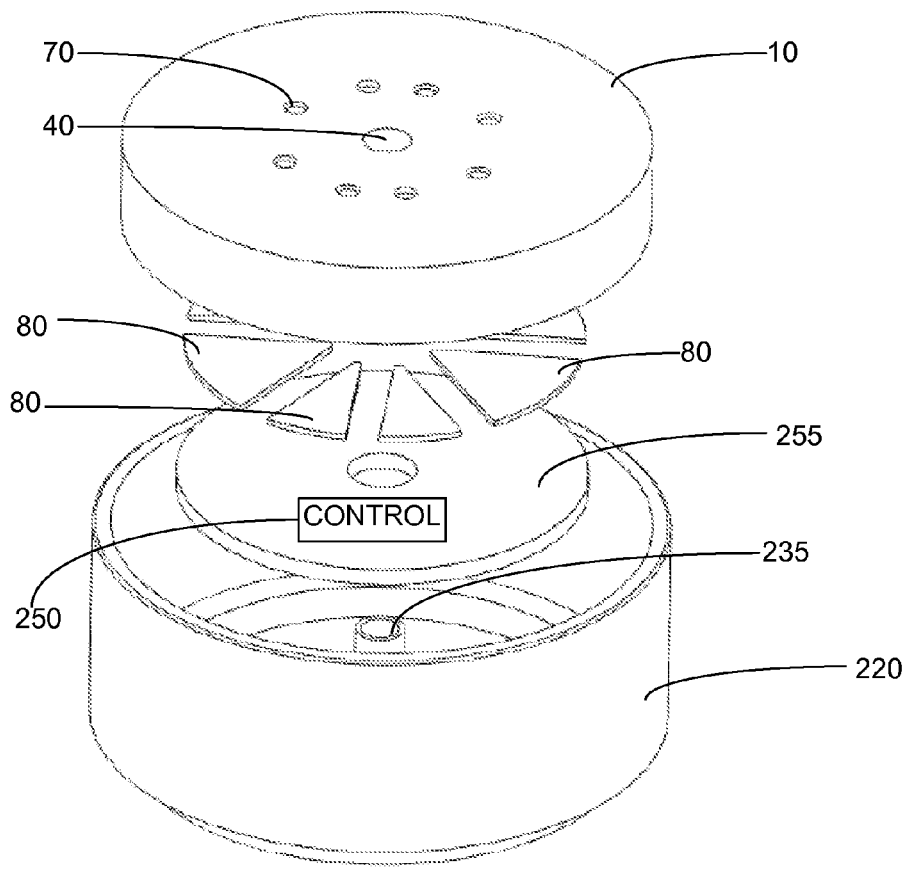
Figure 2E:
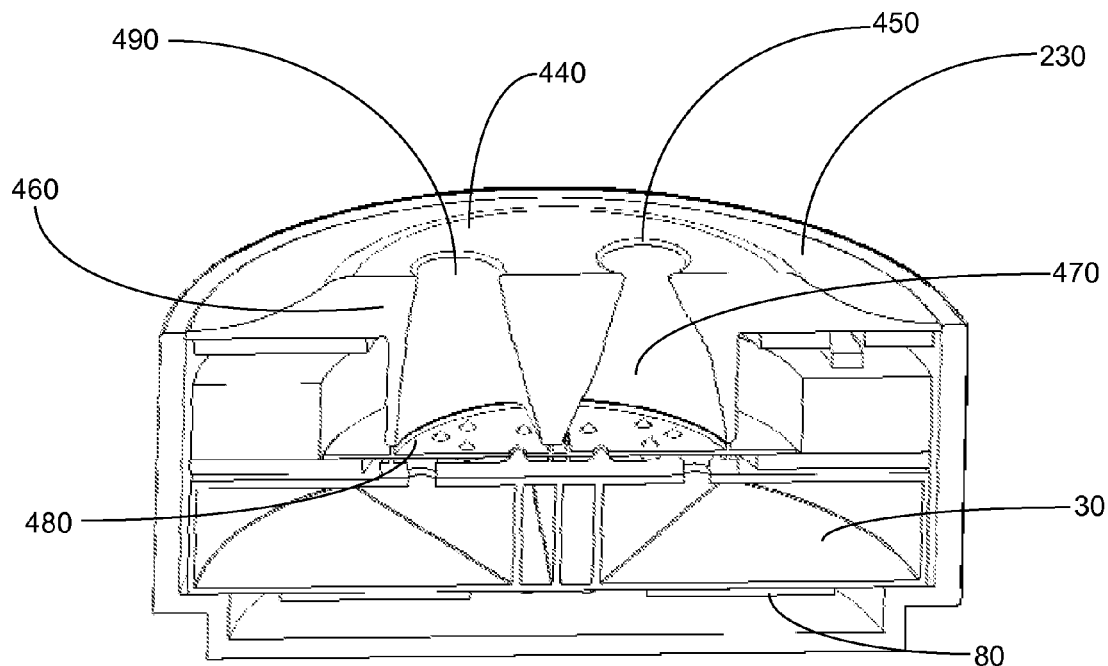
Figure 2F:
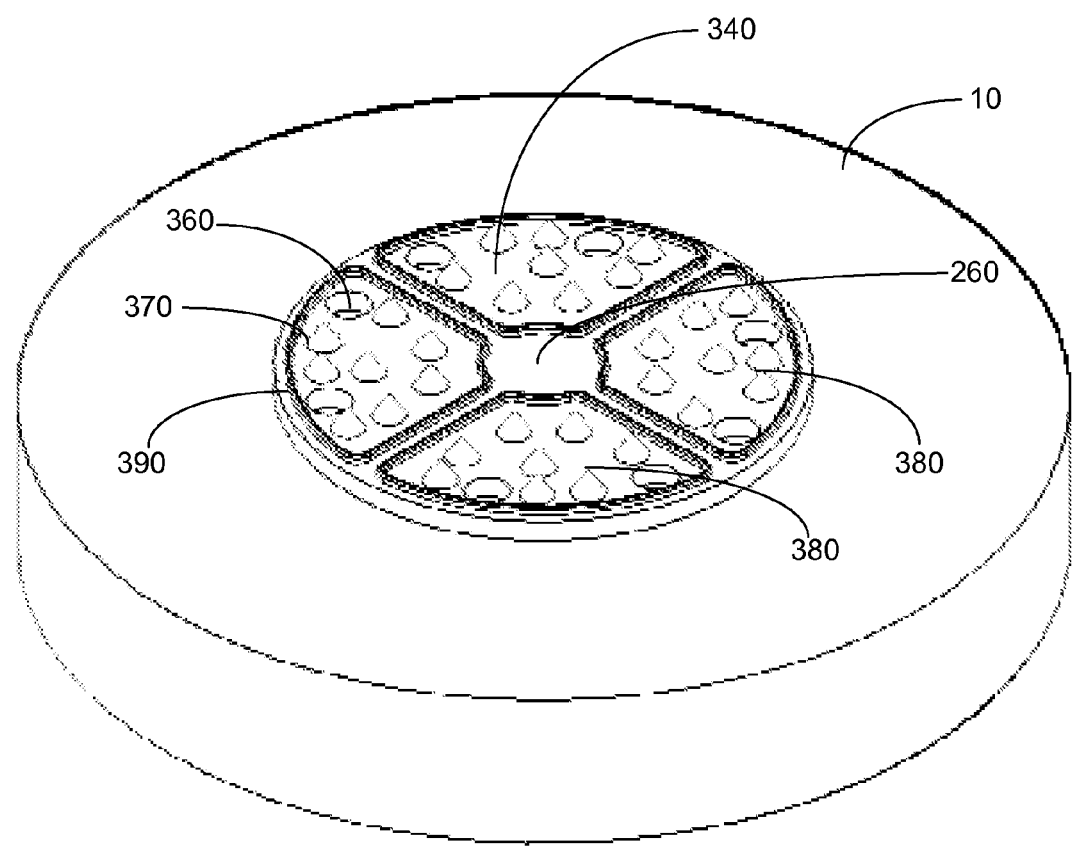
Figure 2G:
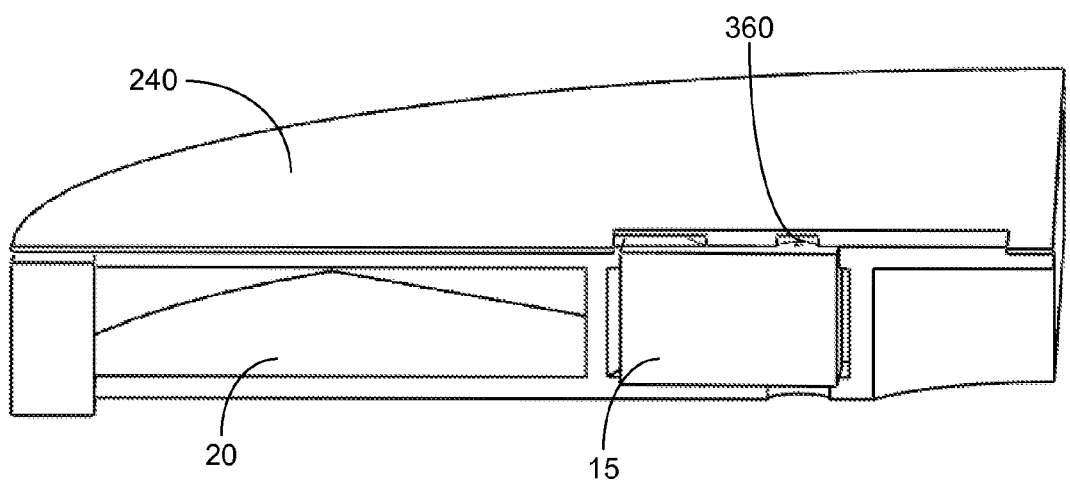

FIGS. 2A-2G illustrate various exploded views of an exemplary embodiment of a scent producing apparatus 200, the figures being taken together. FIG. 2A illustrates a perspective view of scent producing apparatus 200; FIG. 2B illustrates a side cut view of scent producing apparatus 200; FIG. 2C illustrates a perspective view of various components of scent producing apparatus 200; FIG. 2D illustrates a perspective view of various components of scent producing apparatus 200, including a control circuitry; FIG. 2E illustrates a side cut view of various components of scent producing apparatus 200; FIG. 2F illustrates a perspective view of a multi-scent cartridge 10 with a segmented atomizer base connected thereto; and FIG. 2G illustrates a side cut view of a portion of scent producing apparatus 200.

Scent producing apparatus 200 comprises: a first housing 210, forming a reservoir 215; a second housing 220; a segmented nozzle device 230; and a first housing extension 235, exhibiting a plurality of holes 237. Second housing 220 comprises: a multi-scent cartridge 10; the plurality of controllable release mechanisms 80 of FIGS. 1A-1J; an atomizer 240; and a control circuitry 250, placed on a printed circuit board (PCB) 255. Atomizer 240 comprises: a segmented atomizer base 260; a segmented plate 270; a transfer plate 290; a translation and vibration mechanism 280, implemented as a piezo-electric ring; and a locking ring 300, exhibiting a plurality of slits 310 extending from a first face 320 to a second face 330. In one embodiment, translation and vibration mechanism 280 is ring shaped.

Segmented atomizer base 260 comprises a plurality of segments 340. Each segment 340 exhibits a plurality of capillary channels 360 and comprises a plurality of micro-needles 370 extending longitudinally from segment 340 to a tip end 380, each micro-needle 370 forming the needle section of a respective micro-valve. The construction and operation of capillary channels 360 is as described in U.S. Pat. No. 4,301,093 issued on Nov. 17, 1981 to Eck, the entire contents of which are incorporated herein by reference. Each segment 340 is surrounded by a seal 390, preferably constituted of a compliant material, extending longitudinally from segmented atomizer base 260 and rising above segment 340. In one embodiment, the base diameter of each of the plurality of micro-needles 370, defined as where micro-needle 370 meets segment 340, is about 30 microns. Segmented plate 270 comprises a plurality of segments 272, each exhibiting a plurality of perforations 400 extending from a first face 410 to a second face 420, each perforation 400 forming the chassis section of a particular micro-valve, as will be described below. In one embodiment, perforations 400 are separated from each other by a distance of at least 300 microns. Second face 420 of each segment 272 exhibits a border (not shown) arranged to meet the respective seal 390. In one embodiment (not illustrated), translation and vibration mechanism 280 comprises a pair of electrodes arranged to provide electric power to translation and vibration mechanism 280. Locking ring 300 comprises a plurality of locking clamps 430, each protruding through a particular slit 310 from first face 320 to below second face 330 at an acute angle from a longitudinal plane generally defined by first face 320. Segmented nozzle device 230 comprises: a surface 440, exhibiting a plurality of apertures 450; and a nozzle extension 460 comprising a plurality of nozzles 470, each exhibiting an entry port 480 and an exit port 490, with exit port 490 constituted of a particular aperture 450.

Segmented atomizer base 260 is connected to multi-scent cartridge 10 such that each capillary channel 360 is arranged to be in communication with a respective port 70. In further detail, segmented atomizer base 260 is arranged such that each segment 340 is in communication with a particular scent reservoir 20 and one of the plurality of solvent reservoirs 30 via the respective capillary channels 360 and ports 70. In the embodiment where, as described above, a plurality of scent drop on demand units 15 and solvent drop on demand units are provided, segmented atomizer base 260 is arranged such that each segment 340 is in communication with a particular scent drop on demand unit 15 and one of the plurality of solvent drop on demand units via the respective capillary channels 360 and ports 70, as illustrated in FIG. 2G. In one embodiment, as illustrated in FIG. 2G, segmented atomizer base 260 is arranged such that each capillary channel 360 is in direct contact with the respective port 70. In another embodiment (not shown), each capillary channel 360 is connected to the respective port 70 via a capillary wick. Each of the plurality of controllable release mechanisms 80 is connected to a particular one of the plurality of scent reservoirs 20 and the plurality of solvent reservoirs 30, as described above in relation to FIGS. 1A-1D or to a particular one of the plurality of scent drop on demand units 15 and the plurality of solvent drop on demand units, as described above in relation to FIGS. 1E-1J. In the embodiment where a plurality of scent drop on demand units 15 are provided, each is connected to a particular scent reservoir 20 via a respective feeder channel 25, as described above.

Segmented atomizer base 260 is in communication with segmented plate 270 such that each border of the plurality of segments 272 of segmented plate 270 is arranged to meet seal 390 of a particular one of the plurality of segments 340 of segmented atomizer base 260, creating a sealed space. Each of the plurality of micro-needles 370 is arranged to mate with a respective one of perforations 400, thereby forming a micro-valve, the plurality of micro-valves constituting a micro-valve array. Preferably, a portion of each micro-needle 370, and particularly the portion extending through the respective perforation 400, is conically shaped with an apex extending away from the respective segment 340, particularly from segmented atomizer base 260. Perforations 400 are preferably similarly conically shaped, such that when segmented atomizer base 260 is brought to its closest position in relation to second face 420 of segmented plate 270, each micro-needle 370 is seated against the inner walls of the respective perforation 400, and preferably seated flush against the inner walls of the respective perforation 400. Preferably, perforations 400 exhibit a diameter of about 30 microns at first face 410, matching the diameter of micro-needles 370 when completely seated therein. A space is created towards second face 420 of the respective segment 272 when each micro-needle 370 is separated from the respective perforation 400, and a ring shaped droplet of volatile scent liquid is formed by the shape of micro-needle 370 in proximity of first face 410.

Translation and vibration mechanism 280 is in communication with segmented plate 270 via transfer plate 290. A first end 500 of second housing 220 is arranged to mate with first housing 210, and a second end 510 of second housing 220 is arranged to mate with segmented nozzle device 230, nozzle extension 460 being placed inside second housing 220 with surface 440 opposing second end 510. Reservoir 215 of first housing 210 is loaded with the common solvent, and first housing extension 235 extends from reservoir 215 to solvent reservoir extension 40.

In one embodiment, scent producing apparatus 200 is provided in a stationary device and advantageously is placed such that segmented nozzle device 230 is pointed in a generally downward direction, thereby solvent reservoirs 30 are constantly refilled by the common solvent in reservoir 215 via first housing extension 235 and solvent reservoir extension 40. In another embodiment, scent producing apparatus 200 is provided in a portable device and solvent reservoirs 30 are automatically refilled when the portable device is placed such that segmented nozzle device 230 is pointed in a generally downward direction. In order to prevent common solvent from pouring out of solvent reservoirs 30 into reservoir 215 when the portable device is placed such that segmented nozzle device 230 is pointed in a generally upward direction, one of solvent reservoir extension 40 and first housing extension 235 comprises a one-way valve (not shown) blocking the flow of common solvent from solvent reservoirs 30 into reservoir 215. In another embodiment, housing extension 235 is arranged to automatically refill solvent reservoirs 30, or the solvent drop on demand units, by capillary action.

In one embodiment, first housing 210 is removable and reservoir 215 can be refilled when the common solvent is exhausted. In another embodiment, an opening (not shown) is provided in first housing 210 to allow refilling of reservoir 215 when the common solvent is exhausted. In one embodiment, multi-scent cartridge 10 is removable from scent producing apparatus 200 and can be replaced with a new multi-scent cartridge 10 when one or more scent reservoirs 20 are exhausted of super-concentrated volatile scent liquid. In another embodiment, openings are provided to the plurality of scent reservoirs 20 (not shown) to allow refilling of any of the plurality of scent reservoirs 20 when emptied of super-concentrated volatile scent liquid.

In operation, in order to produce a scent, control circuitry 250 applies a low frequency electric power to a controllable release mechanism 80 connected to a particular scent reservoir 20, or to a particular scent drop on demand unit 15, thereby releasing a controlled quantity of super-concentrated volatile scent liquid through the respective port 70, as described above in relation to FIGS. 1A-1J. The released super-concentrated volatile scent liquid then enters the respective capillary channel 360 of the associated segment 340 of segmented atomizer base 260 by capillary action. Control circuitry 250 further applies a low frequency electric power to the controllable release mechanism 80 connected to the solvent reservoir 30, or the solvent drop on demand unit, adjacent to the particular scent reservoir 20 or scent drop on demand unit 15, thereby releasing a controlled quantity of common solvent through the respective port 70. As described above in relation to FIGS. 1E-1J, in the embodiment where scent drop on demand units 15 and solvent drop on demand units are provided with respective micro-needles 15, an additional DC electric power is supplied to the respective controllable release mechanisms 80. The released common solvent then enters the respective capillary channel 360 of the associated segment 340 of segmented atomizer base 260 by capillary action, the associated segment 340 of the solvent reservoir 30, or of the solvent drop on demand unit, being the same segment 340 as the segment 340 associated with the scent reservoir 20 of the scent drop on demand unit 15. In one embodiment, the controlled quantity of the released common solvent is about 20 times greater than the controlled quantity of the released super-concentrated volatile scent liquid. In one embodiment, the amount of time the low frequency electric power is applied to the respective controllable release mechanism 80 is responsive to the amount of super-concentrated volatile scent liquid and common solvent desired to be released. In one embodiment, the amount of power delivered in the low frequency electric power is responsive to the amount of super-concentrated volatile scent liquid and common solvent desired to be released. The controlled quantity of super-concentrated volatile scent liquid and the controlled quantity of common solvent are trapped in the sealed space created by the associated segment 340 of segmented atomizer base 260 and the associated segment 272 of segmented plate 270, and become mixed together to form a volatile scent liquid, which is atomized by the action of translation and vibration mechanism 280 in cooperation with micro-needles 370 and perforations 400, as described below.

Control circuitry 250 is further arranged to apply a low frequency electric power to translation and vibration mechanism 280, and in response translation and vibration mechanism 280 expands, thereby expanding transfer plate 290 and separating segments 340 of segmented atomizer base 260 from segments 272 of segmented plate 270. After expansion, an additional high frequency electrical signal is further supplied, superimposed on the low frequency electrical signal, thereby vibrating translation and vibration mechanism 280. In an exemplary embodiment the high frequency electrical signal exhibits a frequency range of 150-200 kHz, however this is not meant to be limiting in any way. The preferred conical shape of micro-needles 370 function to focus the acoustical energy supplied by translation and vibration mechanism 280 towards tip ends 380, thereby atomizing the scent liquid in contact with micro-needles 370 and within perforations 400 so as to enter the associated nozzle 470, via the entry port 480, and travel through the nozzle 470 and out through exit port 490, to be scented external of segmented nozzle device 230. Advantageously, the amount of separation between segments 340 of segmented atomizer base 260 and segments 272 of segmented plate 270 may be varied responsive to the viscosity of the scent liquid being atomized or nebulized thus varying the dimensions of the ring shaped aperture produced by micro-needles 370 in cooperation with perforations 400, and thus a single ultrasonic micro-needle unit may be utilized for liquids having a wide range of viscosity without being blocked. In one embodiment, when segments 340 of segmented atomizer base 260 are separated from segments 272 of segmented plate 270 by the maximum amount, the borders of segments 272 remain in contact with the respective seals 390 of segments 340 of segmented atomizer base 260.

In one embodiment, the low frequency electric power is not supplied to translation and vibration mechanism 280. Advantageously, the supplied high frequency electric power causes translation and vibration mechanism 280 to vibrate with sufficient amplitude so as to separate segments 340 of segmented atomizer base 260 from segments 272 of segmented plate 270, thus allowing scent liquid to enter perforations 400 and be atomized.

In order to cease the production of the scent, control circuitry 250 is arranged to disconnect any electrical signal from translation and vibration mechanism 280, and in response translation and vibration mechanism 280 contracts, thereby transfer plate 290 contracts, bringing segments 340 of segmented atomizer base 260 into closer proximity with segments 272 of segmented plate 270, until micro-needles 370 are seated within perforations 400, i.e. in a closed position, thus sealing the volatile scent liquid from first face 410, and preventing any further scent from being experienced external of first face 410. Optionally, micro-needles 370 are seated flush within perforations 400 when in the closed position The particular conical shape mentioned above results in a complete seal, which is preferred for use with a volatile scent liquid, however this is not meant to be limiting in any way. In another embodiment a complete seal is not required, but only that the plurality of micro-needles 370 travel sufficiently through perforations 400 to ensure that no residual liquid remains within perforations 400 to prevent occlusion.

In order to produce a compound scent, control circuitry 250 applies a low frequency electric power, and optionally a DC electric power as described above, to a plurality of controllable release mechanisms 80, each connected to a different scent reservoir 20 or scent drop on demand unit 15, thereby releasing controlled quantities of different super-concentrated volatile scent liquids through the respective ports 70 of the associated segments 340 of segmented atomizer base 260, as described above. In one embodiment, each of the different super-concentrated volatile scent liquids produces a unique scent. Control circuitry 250 further applies a low frequency electric power to the controllable release mechanisms 80 connected to respective solvent reservoirs 30, or a respective solvent drop on demand unit, adjacent to the plurality of scent reservoirs 20 or scent drop on demand units 15, thereby releasing controlled quantities of common solvent through the respective capillary channels 360 of the associated segments 340 of segmented atomizer base 260, as described above. A plurality of scents is then produced, as described above, each scent exiting a respective nozzle 470. The plurality of scents mix as they exit the respective nozzles 470, thereby creating a compound scent.

Thus, the single atomizer 240 is arranged to produce any of a plurality of scents responsive to the received super-concentrated volatile scent liquid from the respective scent reservoirs 20 or the respective scent drop on demand units 15. In the event that a plurality of scent reservoirs 20, or scent drop on demand units 15, are simultaneously activated, each of the super-concentrated volatile scent liquid are mixed with solvent from the respective solvent reservoir 30, or solvent drop on demand unit, and atomized by the respective segment of the single atomizer 340. Blending of the scents occurs in the free air after exiting the respective nozzles 270.

Use of a single reservoir 215 for the common solvent allows for miniaturization, since any of the scent reservoirs 20, or scent drop on demand units 15, may be utilized until exhaustion of the contained super-concentrated volatile scent liquid, while receiving solvent from the common reservoir 215.

Advantageously, each of the various atomized volatile scent liquids in combination with the common solvent meet externally of the respective exit port 490, and are not mixed within scent producing apparatus 200. In particular, each of the scents from the respective scent reservoirs 20, or scent drop on demand units 15, are kept isolated from other scents by the operation of the various segments 340 and segmented nozzle device 230. Thus, production of a particular scent is not contaminated by other scents not being produced which may remain on the inner walls of segmented nozzle device 230.

In one embodiment, as will be described below in relation to FIGS. 3A-3G, a neutralizing agent is provided in addition to, or in place of the common solvent. The produced scent thus exhibits a pre-determined persistency and advantageously the scent released by scent producing apparatus 200 does not persist in the vicinity of scent producing apparatus 200 for more than a pre-determined amount of time and therefore a newly produced scent does not mix with previous scents.

Figure 3A:
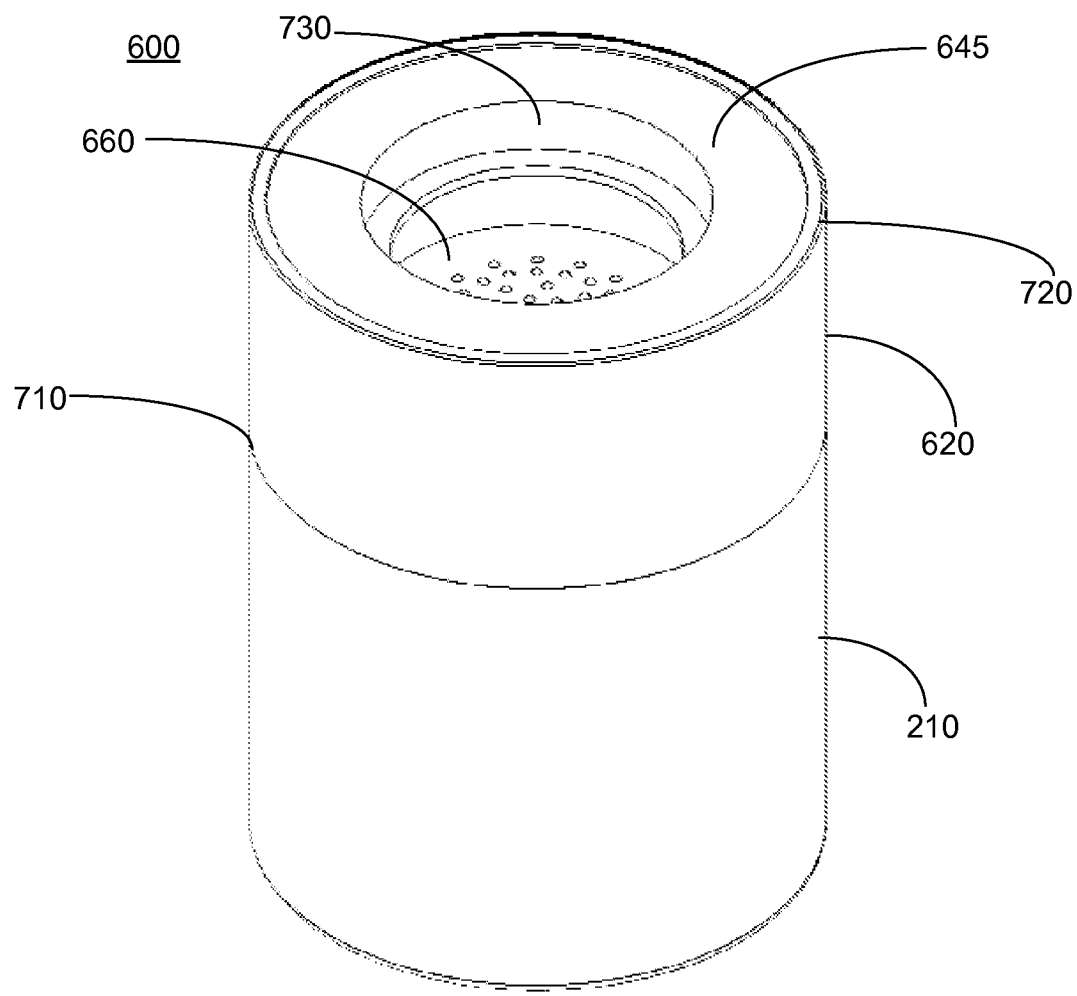
FIGS. 3A-3G illustrate a plurality of exploded views of a scent producing apparatus comprising an atomizer, an extended solvent reservoir and a multi-scent cartridge.
Figure 3B:
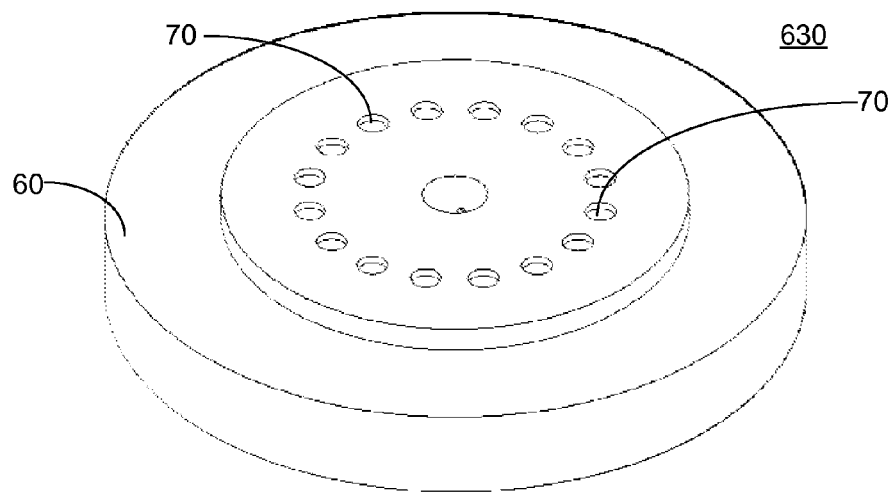
Figure 3C:
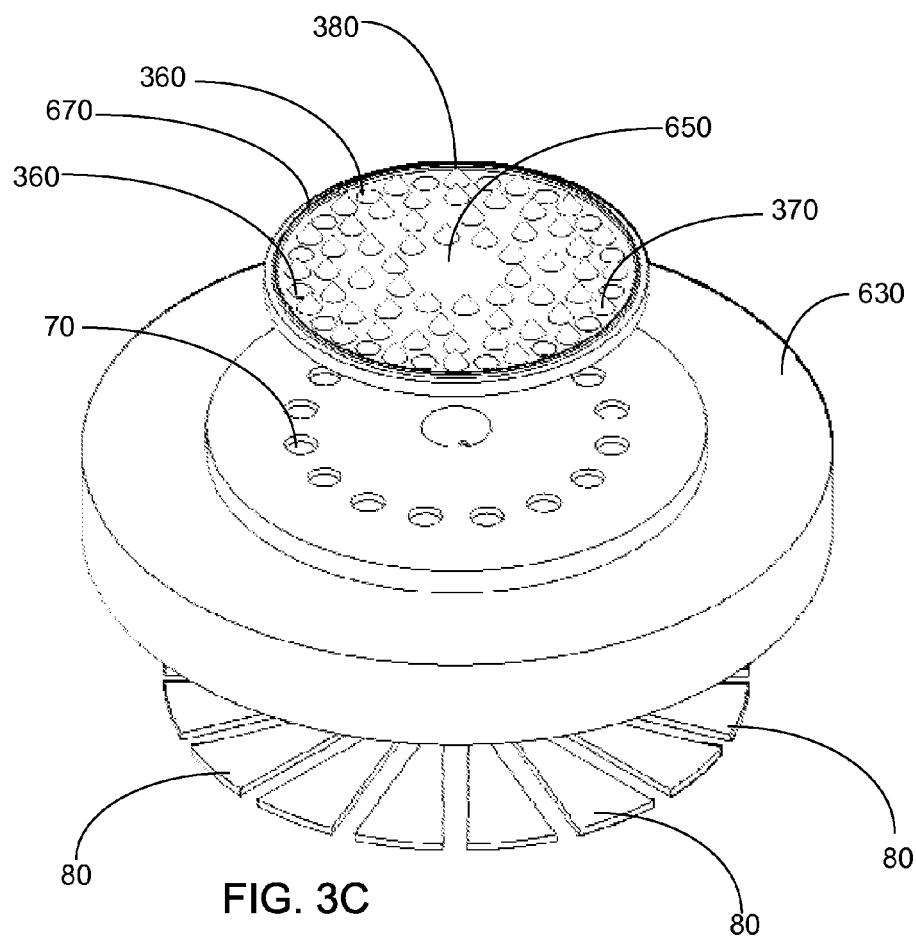
Figure 3D:
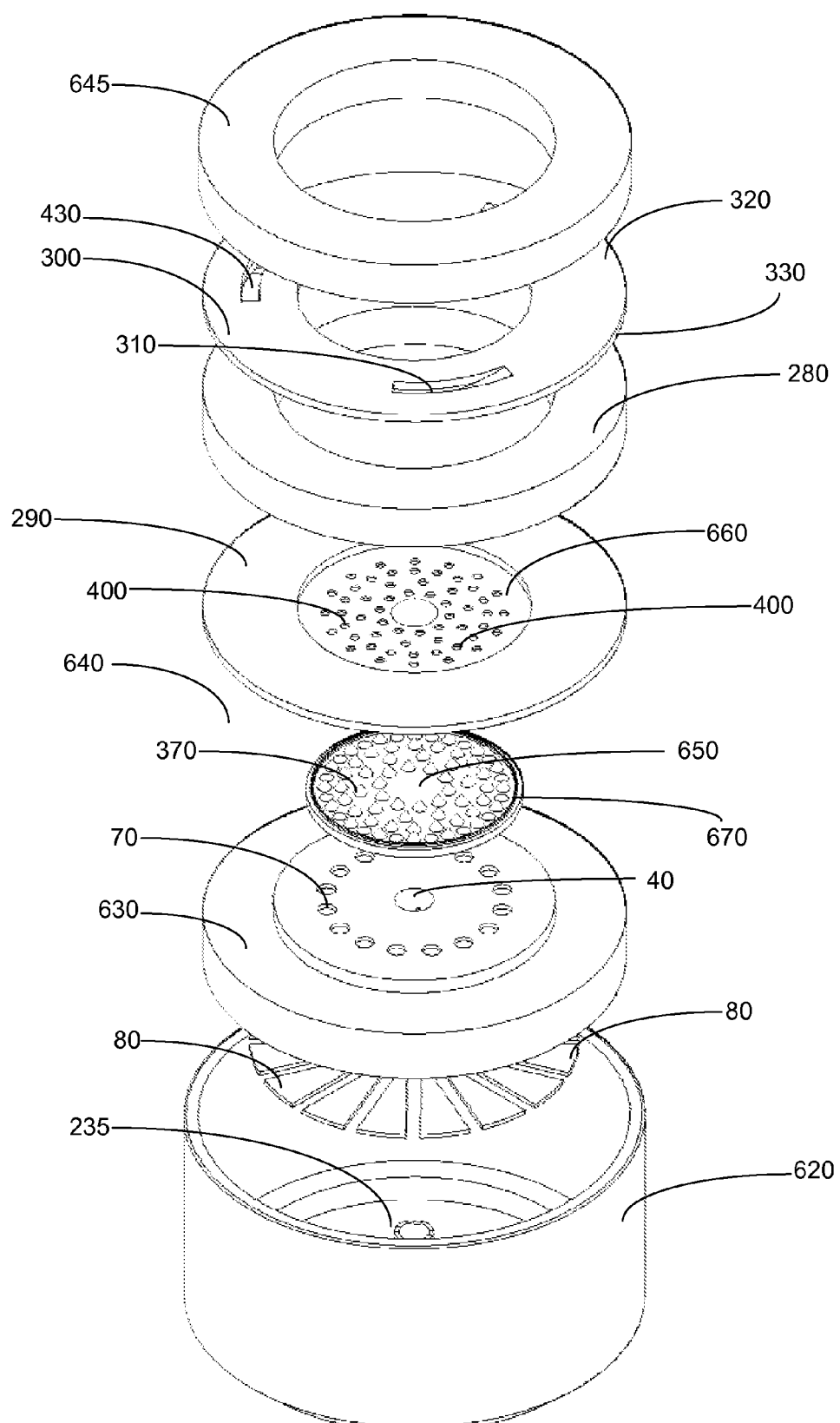
Figure 3E:
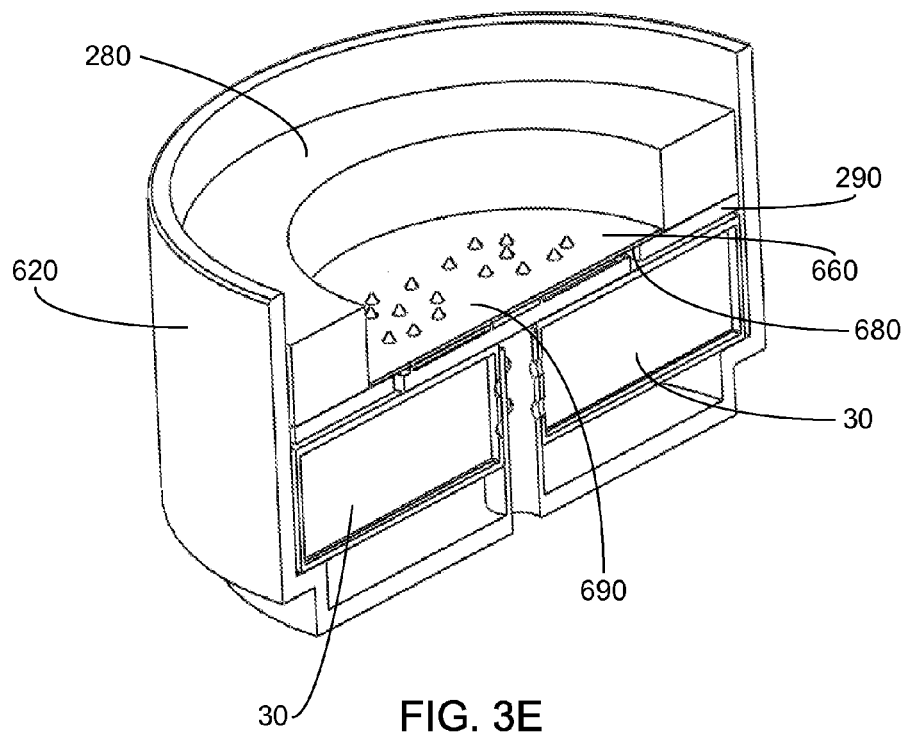
Figure 3F:
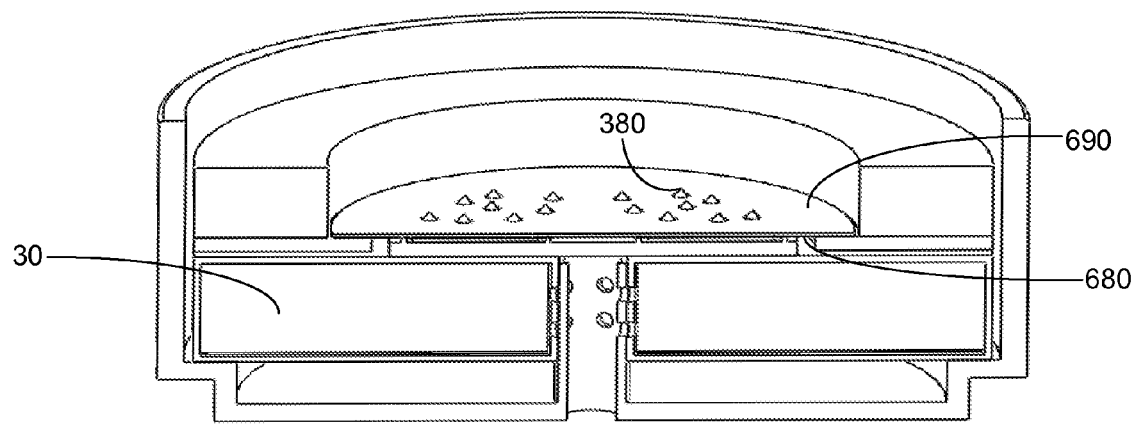
Figure 3G:
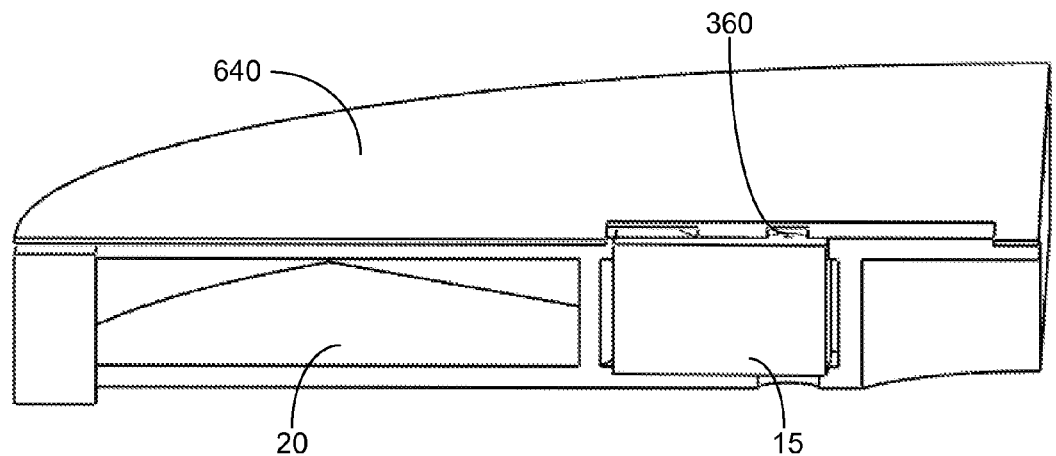

FIGS. 3A-3G illustrate various views of an exemplary embodiment of a scent producing apparatus 600, the figures being taken together. FIG. 3A illustrates a perspective view of scent producing apparatus 600; FIG. 3B illustrates a perspective view of a multi-scent cartridge 630; FIG. 3C illustrates a perspective view of various components of scent producing apparatus 600; FIG. 3D illustrates a perspective view of various components of scent producing apparatus 600; FIG. 3E illustrates a first side cut view of various components of scent producing apparatus 600; FIG. 3F illustrates a second side cut view of various components of scent producing apparatus 600; and FIG. 3G illustrates a side cut view of a portion of scent producing apparatus 600. Scent producing apparatus 600 comprises: a first housing 210; a second housing 620; and a first housing extension 235. Second housing 620 comprises: multi-scent cartridge 630; a plurality of controllable release mechanisms 80; an atomizer 640; a control circuitry 250 (not shown); and a sealing ring 645. Atomizer 640 comprises: a needle base 650; a plate 660; a translation and vibration mechanism 280; a transfer plate 290; and a locking ring 300, exhibiting a plurality of slits 310 extending from a first face 320 to a second face 330. In one embodiment, translation and vibration mechanism 280 comprises a piezoelectric element. In one embodiment, translation and vibration mechanism 280 is ring shaped.

Needle base 650 exhibits a plurality of capillary channels 360 and comprises a plurality of micro-needles 370 extending longitudinally from needle base 650 to a tip end 380, each micro-needle 370 forming the needle section of a respective micro-valve. Needle base 650 is surrounded by a seal 670, preferably constituted of a compliant material, extending longitudinally from needle base 650. In one embodiment, the base diameter of each of the plurality of micro-needles 370 is about 30 microns, the base defined in the direction of needle base 650. Plate 660 exhibits a plurality of perforations 400 extending from a first face 680 to a second face 690, each perforation 400 forming the chassis section of a particular micro-valve, as will be described below. In one embodiment, perorations 400 are separated from each other by at least 300 microns. Locking ring 300 comprises a plurality of locking clamps 430, each protruding through a particular slit 310 from first face 320 to below second face 330 at an acute angle from a longitudinal plane generally defined by first face 320. Locking ring 300 is arranged to secure vibration and translation mechanism 280. Sealing ring 645 is connected to first face 320 of locking ring 300, defining an end of scent producing apparatus 600.

Multi-scent cartridge 630 is in all respects similar to multi-scent cartridge 10 with the exception that a solvent reservoir 30 does not need to be adjacent to every scent reservoir 20 and in the embodiment where a scent drop on demand units 15 and the solvent drop on demand units are provided, a solvent drop on demand unit does not need to be adjacent to every scent drop on demand unit. Advantageously, this allows for the placement of a greater number of scent reservoirs 20 in multi-scent cartridge 630 than in multi-scent cartridge 10. One or more solvent reservoirs 30, or solvent drop on demand units, (not shown), as described above in relation to FIGS. 1A-1J, are provided and placed anywhere in multi-scent cartridge 630. In one embodiment only a single solvent reservoir 30, or solvent drop on demand unit, is provided. In another embodiment a plurality of solvent reservoirs 30, or a plurality of solvent drop on demand units, are provided evenly distributed in multi-scent cartridge 630. Needle base 260 is connected to multi-scent cartridge 630 such that each capillary channel 360 is in communication with a respective port 70 of outer shell 60. In one embodiment, as illustrated in FIG. 3G, needle base 260 is arranged such that each capillary channel 360 is in direct contact with the respective port 70. In another embodiment (not shown), each capillary channel 360 is connected to the respective port 70 via a capillary wick. Each of the plurality of controllable release mechanisms 80 is connected to a particular one of the plurality of scent reservoirs 20 and the plurality of solvent reservoirs 30, as described above in relation to FIGS. 1A-1D, or to a particular one of the plurality of scent drop on demand units 15 and the plurality of solvent drop on demand units, as described above in relation to FIGS. 1E-1J.

Needle base 650 is in communication with plate 660 such that first face 680 of plate 660 is arranged to meet seal 670 of needle base 650, creating a sealed space. Each of the plurality of micro-needles 370 is arranged to mate with a respective one of perforations 400, thereby forming a micro-valve, the plurality of micro-valves constituting a micro-valve array. Preferably, a portion of each micro-needle 370, and particularly the portion extending through perforations 400 are conically shaped with an apex extending away from needle base 650. Perforations 400 are preferably similarly conically shaped, such that when needle base 650 is brought to its closest position in relation to first face 680 of plate 660, each micro-needle 370 is seated against the inner walls of the respective perforation 400. Optionally, each micro-needle 370 is seated flush against the inner walls of the respective perforation 400. Preferably, perforations 400 exhibit a diameter of about 30 microns at first face 680, matching the diameter of micro-needles 370 when completely seated therein. A space is created towards second face 690 of plate 660 when each micro-needle 370 is separated from the respective perforation 400, and a ring shaped droplet of volatile scent liquid is formed by the shape of micro-needle 370 in proximity of second face 690.

Translation and vibration mechanism 280 is in communication with plate 660 via transfer plate 290. A first end 710 of second housing 620 is arranged to mate with first housing 210, and a second end 720 of second housing 620 opposing first end 710 exhibits an aperture 730. In one embodiment, the inner diameter of aperture 730 is equal to the diameter of needle base 650. First housing 210 forms a reservoir 215, as seen in FIG. 2B, arranged to receive the common solvent and a first housing extension 235 extends from the reservoir of first housing 210 to solvent reservoir extension 40 (not shown), as described above in relation to FIGS. 1A-1J.

In one embodiment, scent producing apparatus 600 is provided in a stationary device and advantageously is placed such that aperture 730 is pointed in a generally downward direction, thereby solvent reservoirs 30 are constantly refilled by the common solvent in reservoir 215 via first housing extension 235 and solvent reservoir extension 40. In another embodiment, scent producing apparatus 600 is provided in a portable device and solvent reservoirs 30 are automatically refilled when the portable device is placed such that aperture 730 is pointed in a generally downward direction. In order to prevent common solvent from pouring out of solvent reservoirs 30 into reservoir 215 when the portable device is placed such that aperture 730 is pointed in a generally upward direction, one of solvent reservoir extension 40 and first housing extension 235 comprises a one-way valve (not shown) blocking the flow of common solvent from solvent reservoirs 30 into first housing 210, as described above in relation to scent producing apparatus 200. In another embodiment, as described above, housing extension 235 is arranged to automatically refill solvent reservoirs 30, or the solvent drop on demand units, by capillary action.

In one embodiment, first housing 210 is removable and reservoir 215 can be refilled when exhausted of common solvent. In another embodiment, an opening (not shown) is provided in first housing 210 to allow refilling of reservoir 215 when exhausted of common solvent. In one embodiment, multi-scent cartridge 630 is removable from scent producing apparatus 600 and can be replaced with a new multi-scent cartridge 630 when one or more scent reservoirs 20 are exhausted of super-concentrated volatile scent liquid. In another embodiment, openings are provided to the plurality of scent reservoirs 20 (not shown) to allow refilling of any of the plurality of scent reservoirs 20 when exhausted of super-concentrated volatile scent liquid.

In operation, in order to produce a scent, control circuitry 250 applies a low frequency electric power to a controllable release mechanism 80 connected to a particular scent reservoir 20, or to a particular scent drop on demand unit 15, thereby releasing a controlled quantity of super-concentrated volatile scent liquid through the respective port 70, as described above in relation to FIGS. 1A-1J. The released super-concentrated volatile scent liquid then enters the respective capillary channel 360 of needle base 650 by capillary action. In order to produce a compound scent, control circuitry 250 applies a low frequency electric power to a plurality of controllable release mechanism 80, each connected to a different scent reservoir 20, or scent drop on demand unit 15, thereby releasing controlled quantities of different super-concentrated volatile scent liquids through the respective capillary channels 360 of needle base 650, as described above. In one embodiment, each of the different super-concentrated volatile scent liquids produces a unique scent.

Control circuitry 250 further applies a low frequency electric power to the controllable release mechanism 80 connected to one or more solvent reservoirs 30, or solvent drop on demand units 30, thereby releasing a controlled quantity of common solvent through the respective port 70. The released common solvent then enters the respective capillary channels 360 of needle base 650 by capillary action. In one embodiment, the controlled quantity of common solvent released from the respective solvent reservoirs 30, or solvent drop on demand units, is about 20 times greater than the controlled quantity of the super-concentrated volatile scent liquid released from the respective scent reservoirs 20, or scent drop on demand units 15. In one embodiment, the amount of time the low frequency electric power is applied to the respective controllable release mechanism 80 is responsive to the amount of super-concentrated volatile scent liquid and common solvent desired to be released. In one embodiment, the amount of power delivered in the low frequency electric power is responsive to the amount of super-concentrated volatile scent liquid and common solvent desired to be released. As described above in relation to FIGS. 1E-1J, in the embodiment where scent drop on demand units 15 and solvent drop on demand units are provided with respective micro-needles 15, an additional DC electric power is supplied to the respective controllable release mechanisms 80. The controlled quantity of super-concentrated volatile scent liquid and the controlled quantity of common solvent are trapped in the sealed space created by the needle base 650 and plate 660, and become mixed together to form a scent liquid, which is atomized by the action of translation and vibration mechanism 280 in cooperation with micro-needles 370 and perforations 400, as described above in relation to scent producing apparatus 200.

Production of a scent by scent producing apparatus 600 is in all respects similar to the production of a scent described above in relation to scent producing apparatus 200 and will not be further described for the sake of brevity. The atomized scent liquid exits scent producing apparatus 600 through aperture 730 to be scented external of second housing 620.

After production of a scent is ceased, while micro-needles 370 are seated within perforations 400, a medium to high frequency electrical signal, in one non-limiting embodiment being from 40 kHz to 400 kHz, is supplied to translation and vibration mechanism 280, thus vibrating the combination of plate 660 and micro-needles 370. Any residual volatile scent on tip ends 380 and second face 690 of plate 660 is promptly atomized, or nebulized, and removed completely, thus ceasing scent production, and cleaning the previously issued scent from micro-needles 370, allowing for production of a different subsequent scent without any residual scent from the previous scent production.

Thus, the single atomizer 640 is arranged to produce any of a plurality of scents responsive to the received super-concentrated volatile scent liquid from the respective scent reservoirs 20, or scent drop on demand units 15. In the event that a plurality of scent reservoirs 20, or scent drop on demand units 15, are simultaneously activated, each of the super-concentrated volatile scent liquid are mixed with solvent from the respective solvent reservoir 30, or solvent drop on demand unit, and atomized as a blended scent by atomizer 640.

After scent production, ultrasonic cleaning of atomizer 640 is performed, thus ensuring that a subsequent scent production, or emission, is free from residual scent, as described in the above embodiment. Advantageously, scent producing apparatus 600 can be used to produce a scent, ultrasonically cleaned and used again to produce a different scent.

In another embodiment, multi-scent cartridge 630 is provided with one or more neutralizer reservoirs in place of one or more scent reservoirs 20 and/or solvent reservoirs 30. Each neutralizer reservoir is provided with a neutralizing agent. In one embodiment the neutralizing agent is an amphoteric substance arranged to neutralize any scent produced by scent producing apparatus 600 after a pre-determined time period. In one particular embodiment the neutralzing agent is a sodium bicarbonate solution. In another embodiment the neutralizing agent is a strongly basic liquid, preferably exhibiting a pH of greater than 9, so as to neutralize any acidic volatile scent liquid. In one further embodiment, the common solvent in reservoir 215 is replaced with a neutralizing agent. In one further embodiment, an additional reservoir comprising a neutralizing agent is provided and is arranged to release the neutralizing agent in parallel with, or alternately with, the common solvent. During production of a scent, the neutralizing agent is thus released into atomizer 640 in addition to, or in place of, the common solvent, as described above. As a result, scent is produced in atomizer 640 with a pre-determined persistence. Advantageously, atomizer 640 does not have to be ultrasonically cleaned, as no residual scent lingers in atomizer 640. Further advantageously, the scent released by scent producing apparatus 600 does not persist in the vicinity of scent producing apparatus 600 for more than a pre-determined amount of time and a newly produced scent does not mix with previous scents.

Use of a single reservoir 215 for the common solvent allows for miniaturization, since any of the scent reservoirs 20 may be utilized until exhaustion of the contained super-concentrated volatile scent liquid, while receiving solvent from the common reservoir 215.

Figure 4:
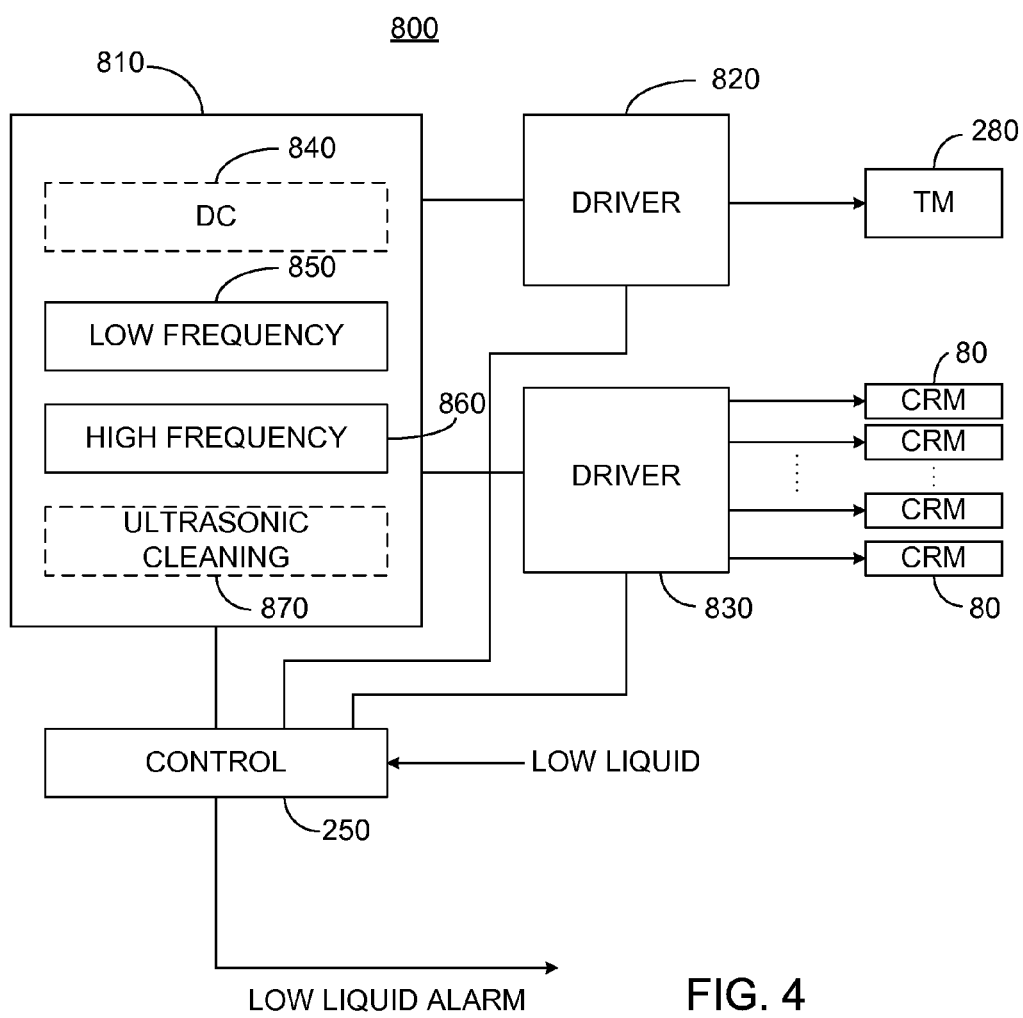
FIG. 4 illustrates a high level schematic diagram of a driving circuitry for controllably driving the scent producing apparatus of FIGS. 2A-2G and the scent producing apparatus of FIGS. 3A-3G.
Figure 5:
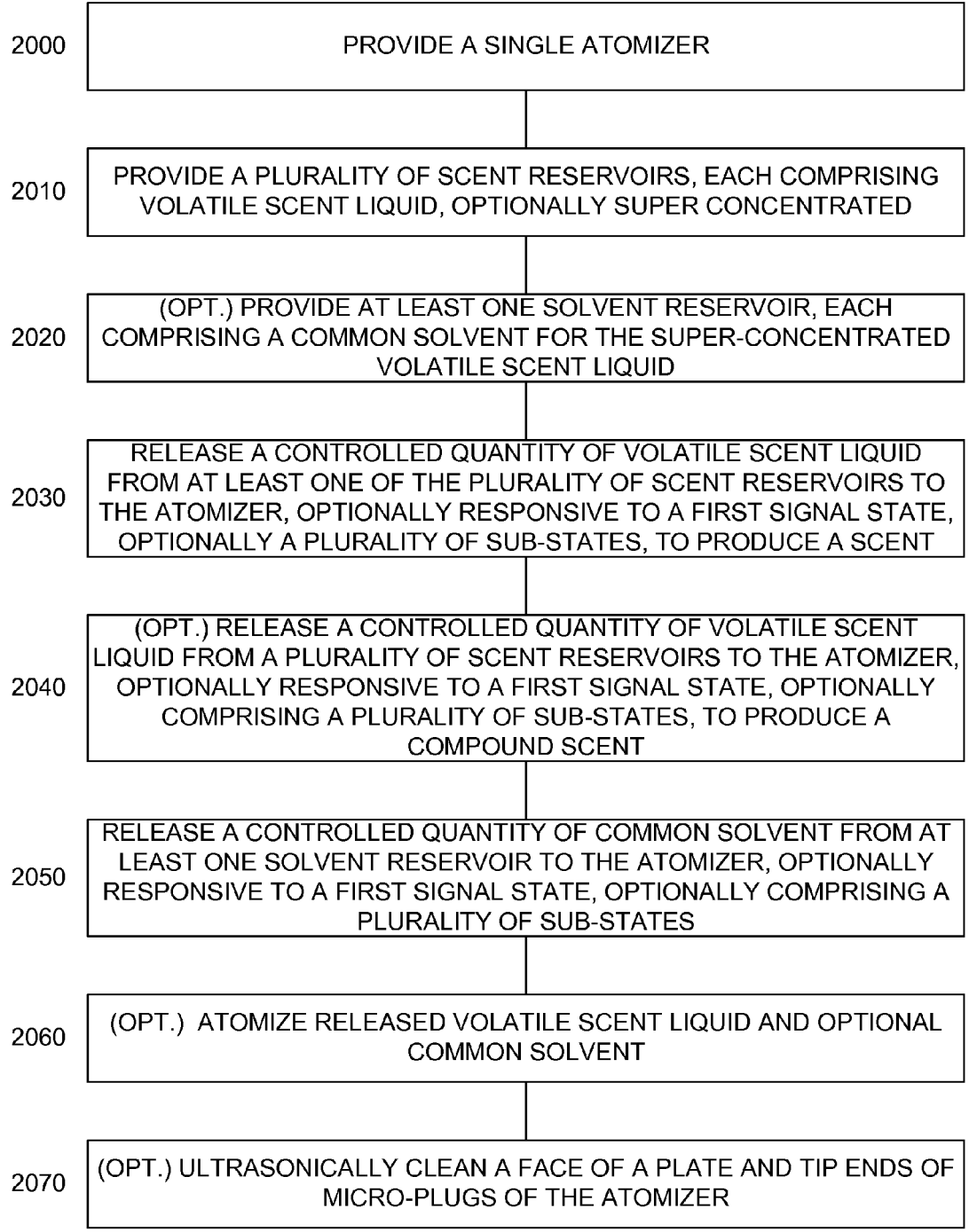
FIG. 5 illustrates a high level flow chart of the operation of the scent producing apparatus of FIGS. 2A-2G.
Figure 6:
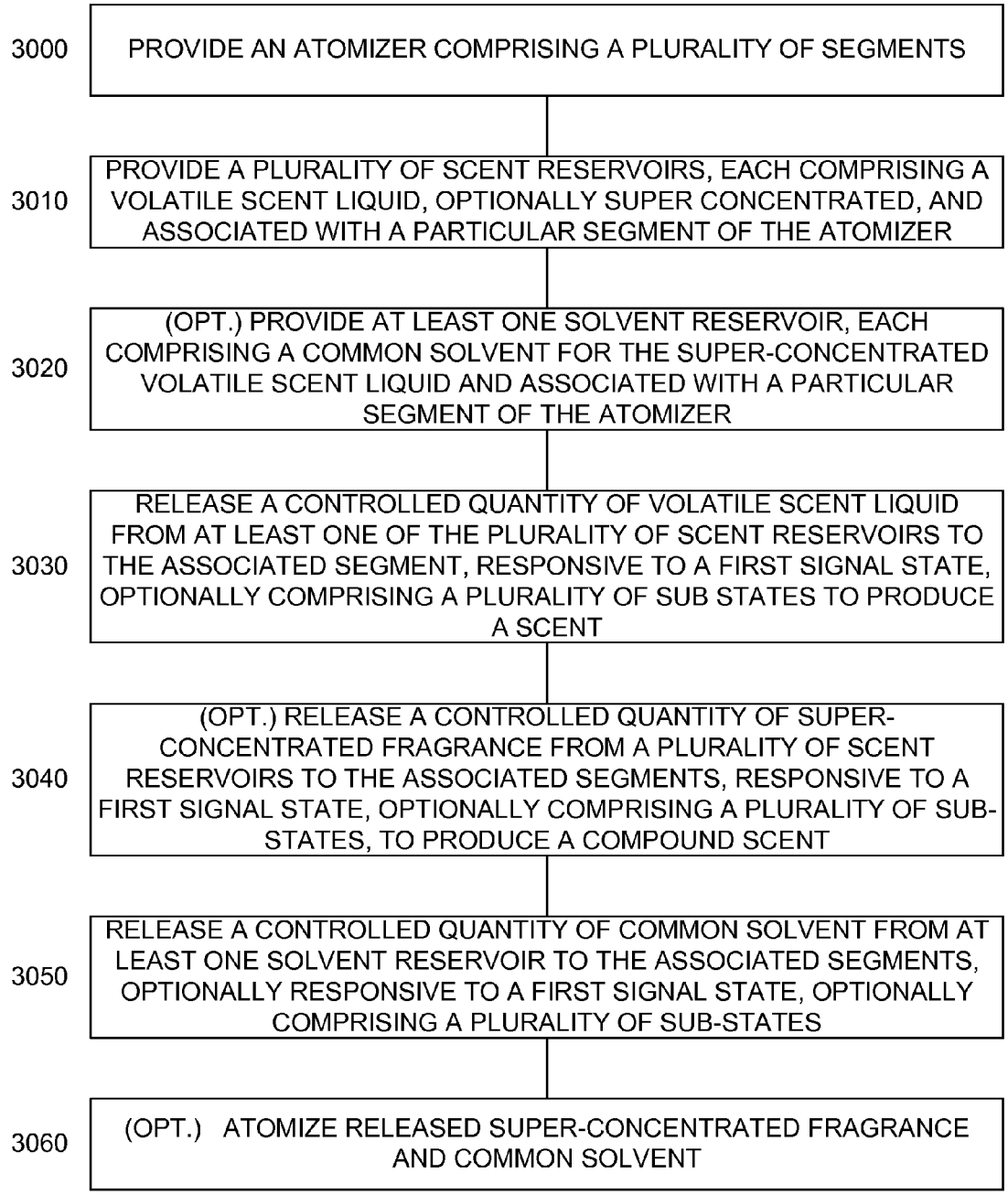
FIG. 6 illustrates a high level flow chart of the operation of the scent producing apparatus of FIGS. 3A-3G.

FIG. 4 illustrates a high level schematic diagram of a driving circuitry 800, comprising: a pulse generator 810; a first driver 820; a second driver 830; a translation and vibration mechanism 280; a plurality of controllable release mechanisms 80; and a control circuitry 250. In one embodiment, driving circuitry 800 is located on a printed circuit board 255 as described above in relation to FIG. 2C. Optionally, a plurality of low liquid sensors each associated with a particular one of the plurality of scent reservoirs 20 and the plurality of solvent reservoirs 30 are further provided in communication with control circuitry 250 and are arranged to output an alarm when a quantity of liquid in the respective reservoir is detected to be less than a predetermined amount. Pulse generator 810 preferably comprises: an optional DC functionality 840; a low frequency functionality 850; a high frequency functionality 860; and an optional ultrasonic cleaning functionality 870. Control circuitry 250 is in communication with each of pulse generator 810, first driver 820 and second driver 830. A first output of pulse generator 810 is connected, via first driver 820, to translation and vibration mechanism 280 and a second output of pulse generator 810 is connected to second driver 830. In the embodiment where translation and vibration mechanism 280 comprises a pair of electrodes, the first output of pulse generator 810 is connected, via first driver 820, to a first of the pair of electrodes. In one embodiment, the first output of pulse generator 810 is connected, via first driver 820, to both of the pair of electrodes, a first of the pair of electrodes being responsive to low frequency functionality 850 and a second of the pair of electrodes being responsive to high frequency functionality 860. Each of a plurality of outputs of second driver 830 is connected to a respective one of the plurality of controllable release mechanisms 80.

In operation, and as described above, control circuitry 250 operates low frequency functionality 850, and optionally optional DC functionality 840, to generate a low frequency electrical signal and an optional DC electric signal, which is driven towards a plurality of controllable release mechanisms 80 by second driver 830, thereby releasing a controlled quantity of super-concentrated volatile scent liquid from at least one scent reservoir 20, or scent drop on demand unit 15, of multi-scent cartridge 10 or 630 and a controlled quantity of common solvent from at least one solvent reservoir 30, or scent drop on demand unit, of multi-scent cartridge 10 or 630. As described above, in one embodiment, the released controlled quantity of common solvent is about 20 times greater than the released controlled quantity of super-concentrated volatile scent liquid. As described above, in one embodiment, the amount of time the low frequency electric power is applied to the respective controllable release mechanism 80 is responsive to the amount of super-concentrated volatile scent liquid and common solvent desired to be released. In one embodiment, the amount of power delivered in the low frequency electric power is responsive to the amount of super-concentrated volatile scent liquid and common solvent desired to be released.

For operation of atomizer 240, as described above in relation to FIGS. 2A-2G, control circuitry 250 further operates low frequency functionality 850 to generate a low frequency electrical signal, which is driven towards translation and vibration mechanism 280 by first driver 820, thereby separating segmented atomizer base 260 from segmented plate 270.

High frequency functionality 860 is arranged to vibrate one or more of segmented plate 270 and segmented atomizer base 260, as described above.

For operation of atomizer 640, as described above in relation to FIGS. 3A-3G, control circuitry 250 further operates low frequency functionality 850 to generate a low frequency electrical signal, which is driven towards translation and vibration mechanism 280 by first driver 820, thereby separating needle base 650 from plate 660. High frequency functionality 860 is arranged to vibrate one or more of plate 660 and needle base 650, as described above. When production of a scent is ceased, as described above, control circuitry 250 operates ultrasonic cleaning functionality 870 to perform ultrasonic cleaning by providing vibrating energy to needle base 650 and plate 660 while seated. In one non-limiting embodiment, ultrasonic cleaning functionality 870 is arranged to output an electric power of 40 kHz to 400 kHz. In one embodiment, ultrasonic cleaning functionality 870 is arranged to perform ultrasonic cleaning in the absence of both low frequency electrical signal from low frequency functionality 850 and high frequency electrical signal from high frequency functionality 860.

As described above, low frequency functionality 850 may be operative to generate a low frequency electrical signal to operate one of segmented atomizer base 260 and needle base 650, respectively as a micro-pump.

FIG. 5 illustrates a high level flow chart of a first method of scent production. In stage 2000, a single atomizer is provided, such as atomizer 640 of FIGS. 3A-3G. In stage 2010, a plurality of scent reservoirs is provided, each in communication with the provided atomizer of stage 2000 and comprising a volatile scent liquid. In one embodiment, the volatile scent liquid is super-concentrated. In optional stage 2020, in the embodiment where the volatile scent liquid of stage 2010 is super-concentrated, at least one solvent reservoir is further provided, each in communication with the provided single atomizer of stage 2000 and comprising a common solvent for the super-concentrated volatile scent liquids of stage 2010.

In stage 2030, a controlled quantity of volatile scent liquid is released from at least one of the provided plurality of scent reservoirs of stage 2010 to the provided single atomizer of stage 2000, thereby producing a scent. Optionally, the volatile scent liquid is released responsive to a first signal state of a control circuitry, such as control circuitry 250. In one embodiment, the volatile scent liquid is released by providing a low frequency electric power to an associated piezoelectric element, as described above in relation to controllable release mechanisms 80, the first signal state being the activated low frequency electric power. Optionally, the first state exhibits a plurality of sub-states each associated with a particularly quantity of volatile scent liquid to be released, in one embodiment the plurality of sub-states comprising a plurality of amplitudes of the low frequency electric power. In optional stage 2040, a controlled quantity of volatile scent liquid is released from each of a plurality of the provided scent reservoirs, responsive to the first state of the electrical signal of stage 2030, each of the volatile scent liquids exhibiting a unique scent, to the provided atomizer, thereby producing a compound, or blended scent within the provided single atomizer of stage 2000.

In optional stage 2050, utilized in cooperation with optional stage 2020, a controlled quantity of the common solvent is released from at least one of the provided solvent reservoirs to the provided atomizer, responsive to a first state of an electrical signal as described above in relation to stage 2030, thereby mixing with the super-concentrated volatile scent liquid. In one embodiment, the common solvent is released by providing a low frequency electric power to an associated piezoelectric element, as described above in relation to controllable release mechanisms 80, the first signal state being the activated low frequency electric power. Optionally, the first signal state exhibits a plurality of sub-states each associated with a particularly quantity of common solvent to be released, in one embodiment the plurality of sub-states comprising a plurality of amplitudes of the low frequency electric power. In one embodiment, the quantity of common solvent released is about 20 times the quantity of the released super-concentrated volatile scent liquids of stage 2030 and optional stage 2040.

In optional stage 2060, the volatile scent liquid, optionally with common solvent, are atomized, as described above in relation to FIGS. 2A-2G, by the single atomizer of stage 2000, preferably the single atomizer comprising a plate and a plurality of micro-needles. In optional stage 2070, after the production of a scent is ceased, a face of the plate and the tip ends of the micro-needles are ultrasonically cleaned, to remove any residual scent, as described above in relation to FIGS. 3A-3G. Advantageously, scent producing apparatus 600 can be used to produce a scent, ultrasonically cleaned and used again to produce a different scent.

FIG. 6 illustrates a high level flow chart of a second method of scent production. In stage 3000, a single atomizer is provided comprising a plurality of segments, such as segments 340 of segmented atomizer base 260, as described above in relation to FIGS. 2A-2G. In stage 3010, a plurality of scent reservoirs is provided, each associated, and in communication, with a particular segment of the provided single atomizer of stage 3000. Each of the provided plurality of scent reservoirs comprises a volatile scent liquid, preferably each of the volatile scent liquids are arranged to produce a unique scent. In one embodiment, the volatile scent liquid is super-concentrated.

In optional stage 3020, in the embodiment where the voltage scent liquid of stage 3010 is super-concentrated, at least one solvent reservoir is further provided, each associated, and in communication, with a particular segment of the provided single atomizer of stage 3000. Each of the at least one solvent reservoir comprises a common solvent for the super-concentrated volatile scent liquids of the scent reservoirs of stage 3010.

In stage 3030, a controlled quantity of volatile scent liquid is released from at least one of the provided plurality of scent reservoirs of stage 3010 to the associated segment of the single provided atomizer of stage 3000, optionally responsive to a first state of an electrical signal, thereby producing a scent. In one embodiment, the volatile scent liquid is released by providing a low frequency electric power to an associated piezoelectric element, as described above in relation to controllable release mechanisms 80, the first signal state being the activated low frequency electric power. Optionally, the first state exhibits a plurality of sub-states each associated with a particularly quantity of volatile scent liquid to be released, in one embodiment the plurality of sub-states comprising a plurality of amplitudes of the low frequency electric power. In optional stage 3040, a controlled quantity of volatile scent liquid is released from a plurality of the provided scent reservoirs of stage 3010, responsive to the first state of the electrical signal of stage 3030, each of the volatile scent liquids exhibiting a unique scent, to the respective associated segments of the provided single atomizer of stage 3000, thereby producing a compound, or blended, scent.

In optional stage 3050, utilized in conjunction with optional stage 3020, a controlled quantity of the common solvent is released from at least one of the provided solvent reservoirs of stage 3020 to the respective associated segments of the provided single atomizer of stage 3000, responsive to a first state of the electrical signal of stage 3030, thereby mixing with the super-concentrated volatile scent liquid. In one embodiment, as described above in relation to FIGS. 2A-2G, a controlled quantity of common solvent is released from a particular solvent reservoir for each scent reservoir with a controlled quantity of super-concentrated volatile scent liquid released therefrom. In one embodiment, the common solvent is released by providing a low frequency electric power to an associated piezoelectric element, as described above in relation to controllable release mechanisms 80, the first signal state being the activated low frequency electric power. Optionally, the first signal state exhibits a plurality of sub-states each associated with a particularly quantity of common solvent to be released, in one embodiment the plurality of sub-states comprising a plurality of amplitudes, or a plurality of duty cycles, of the low frequency electric power. In one embodiment, the quantity of common solvent released is about 20 times the quantity of the released super-concentrated volatile scent liquids of optional stage 3030. In optional stage 3060, the released volatile scent liquid, or liquids, with optional common solvent, are atomized by the provided single atomizer of stage 3000.

Figure 7A:
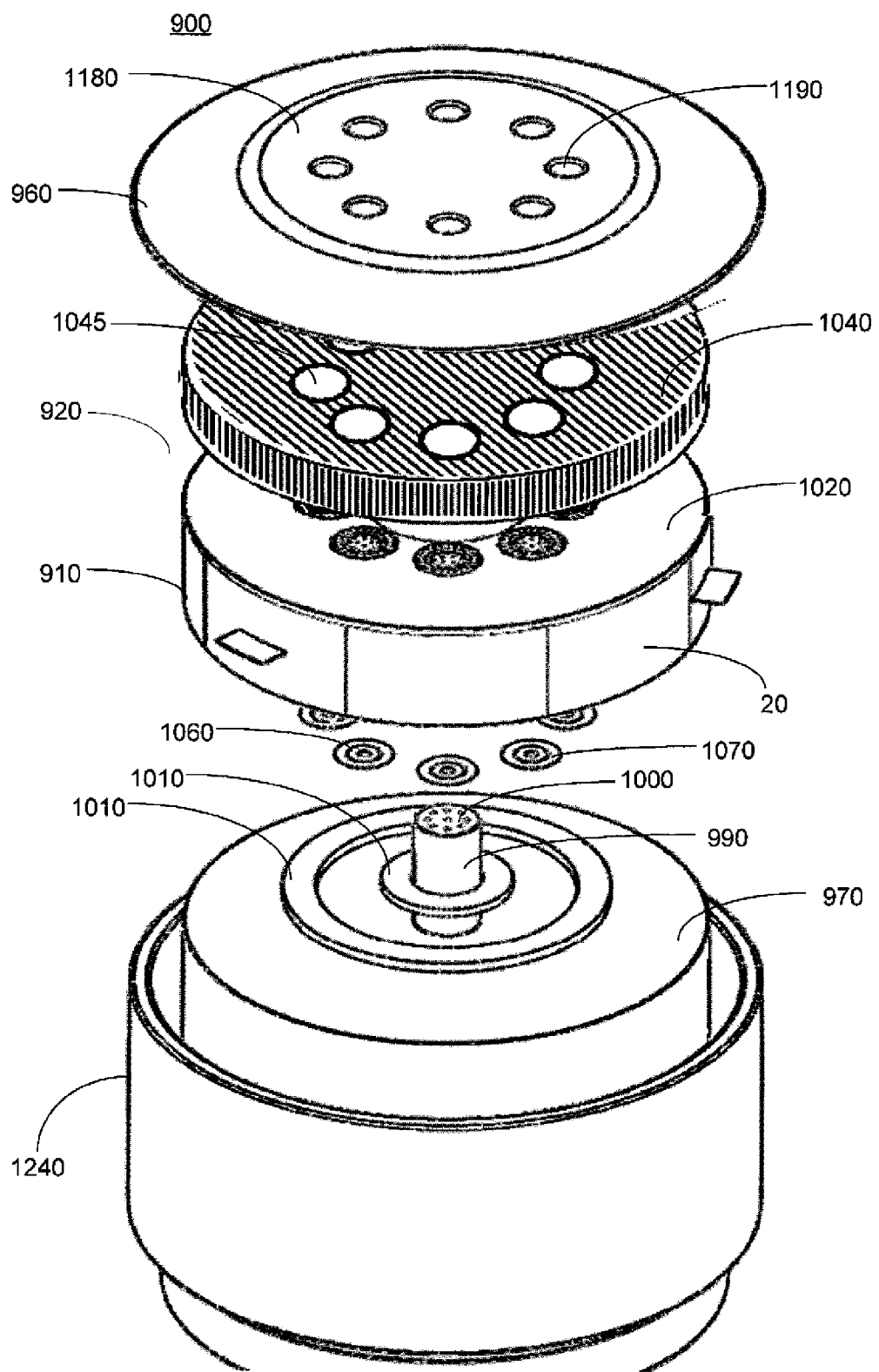
FIGS. 7A-7I illustrate a plurality of views of an exemplary embodiment of a scent producing apparatus comprising a multi-scent cartridge in communication with an atomizer.
Figure 7B:
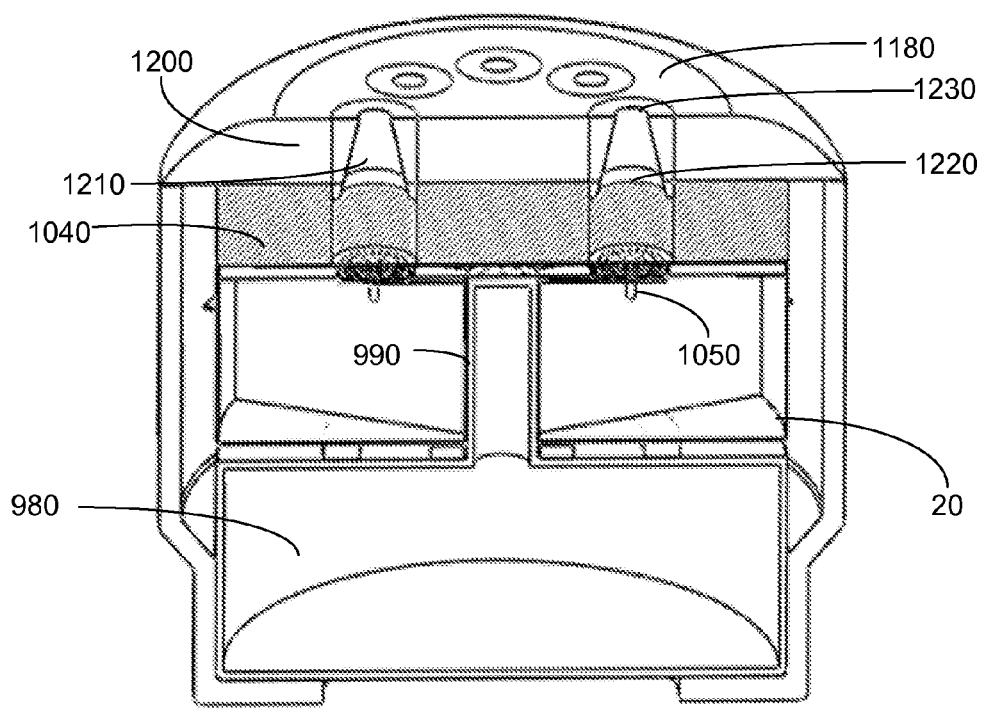
Figure 7C:
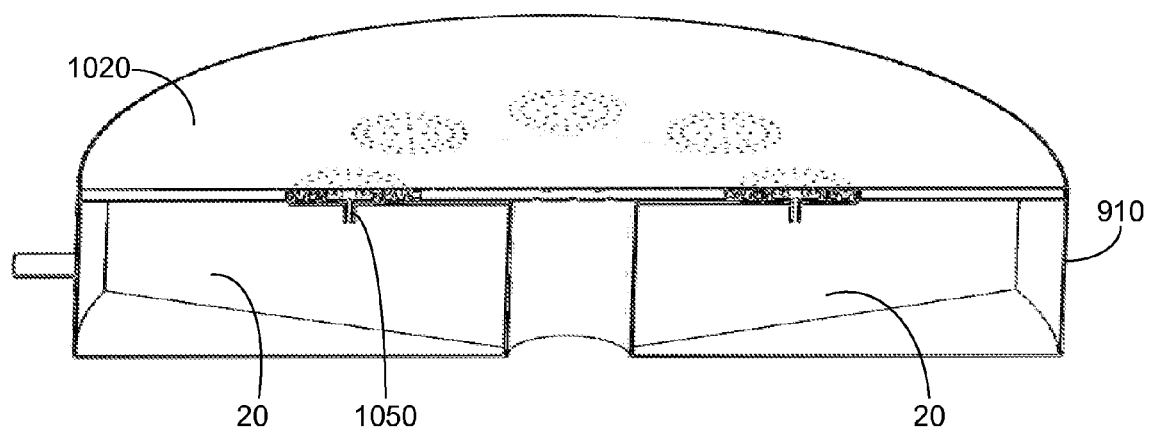
Figure 7D:
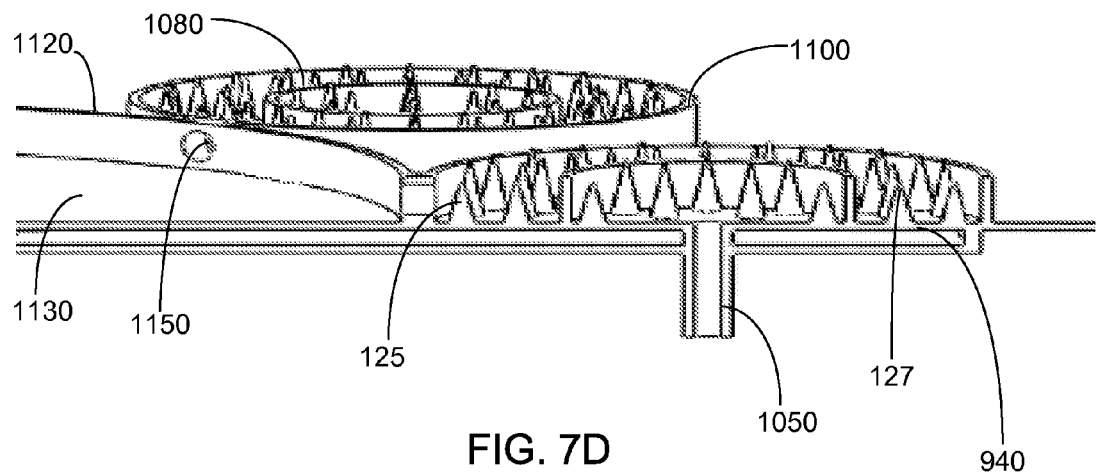
Figure 7E:
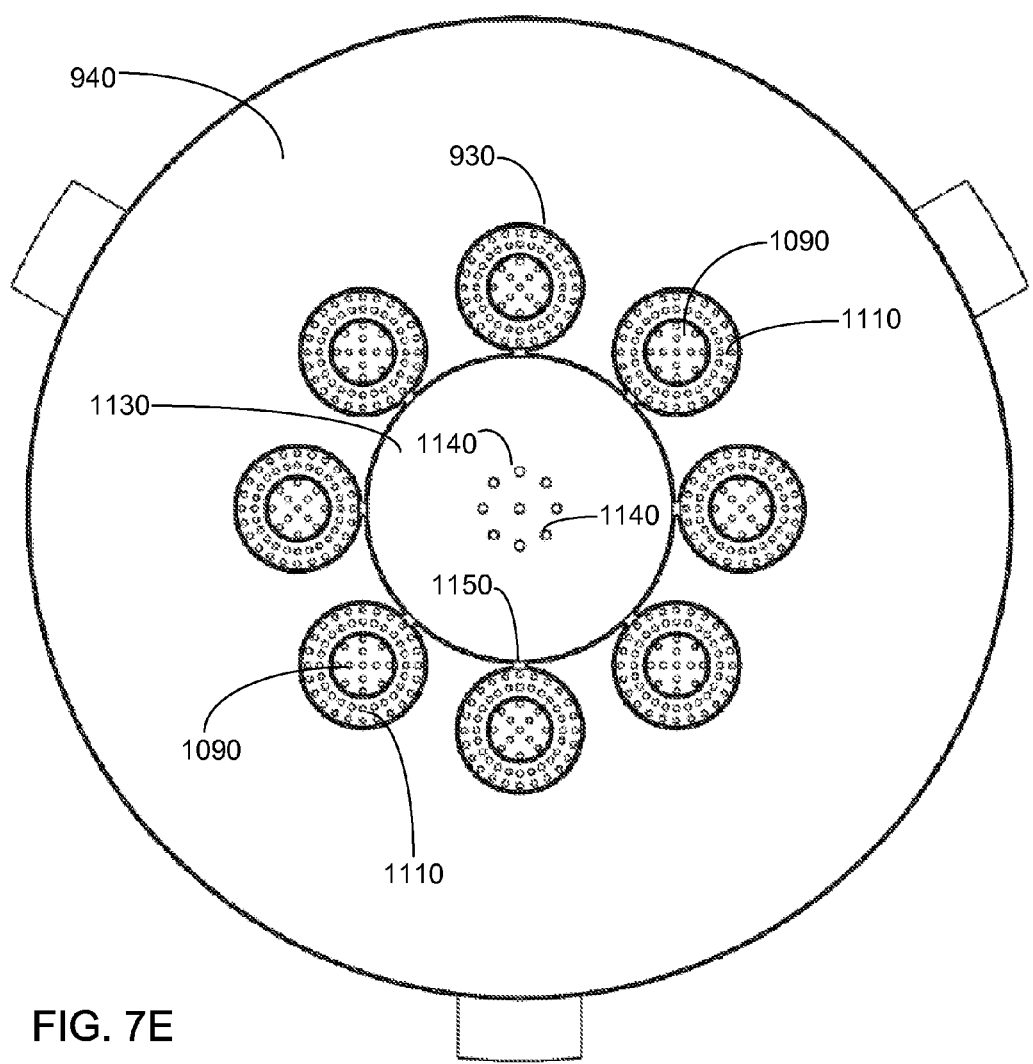
Figure 7F:
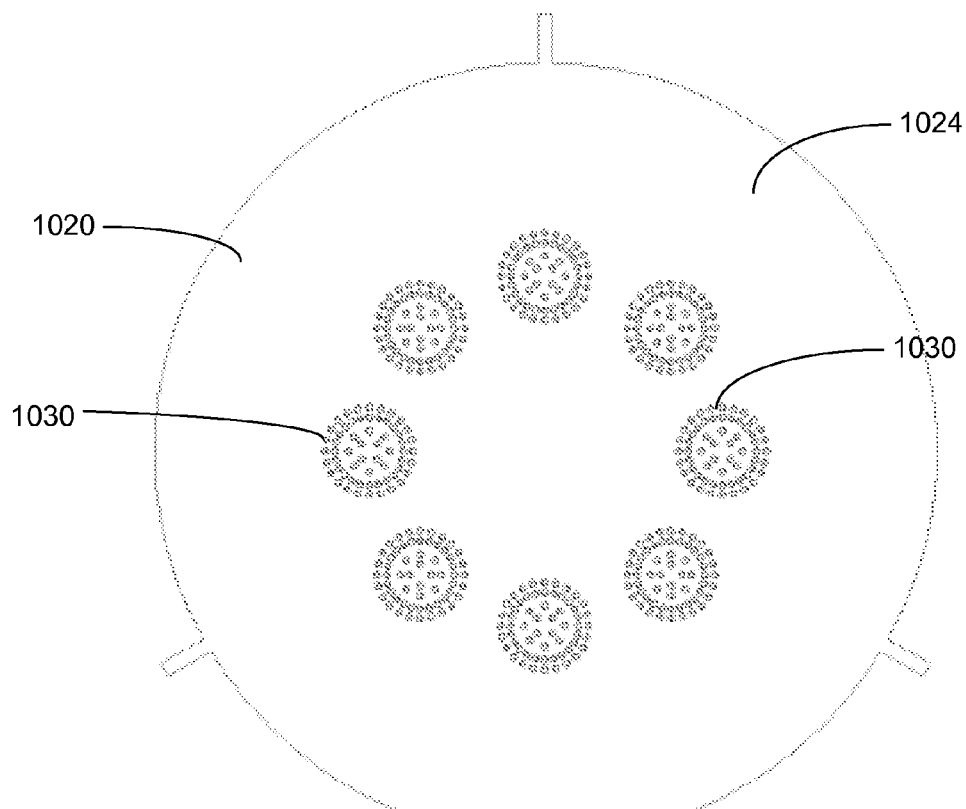
Figure 7G:
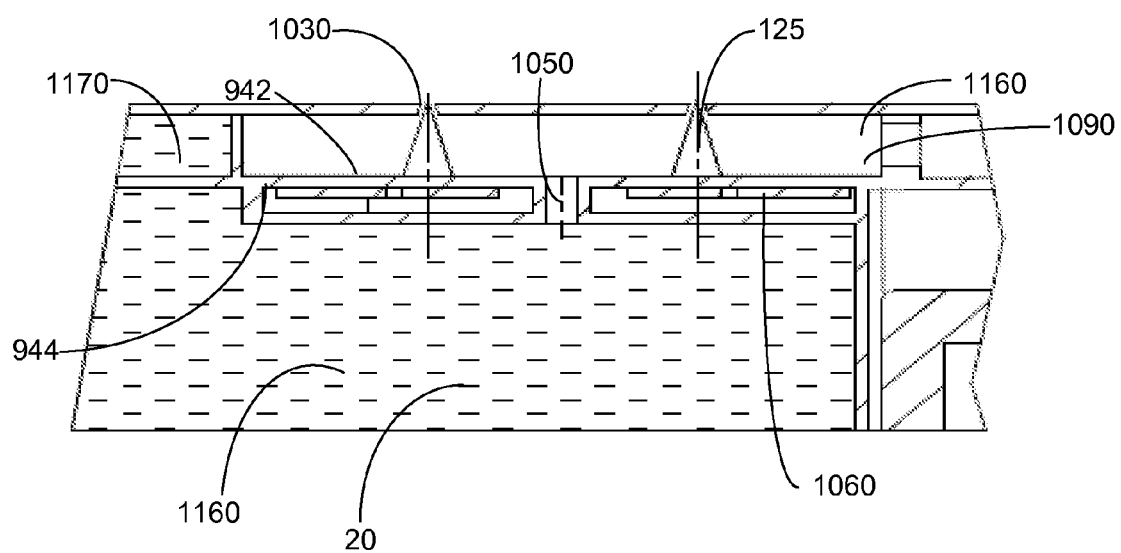
Figure 7H:
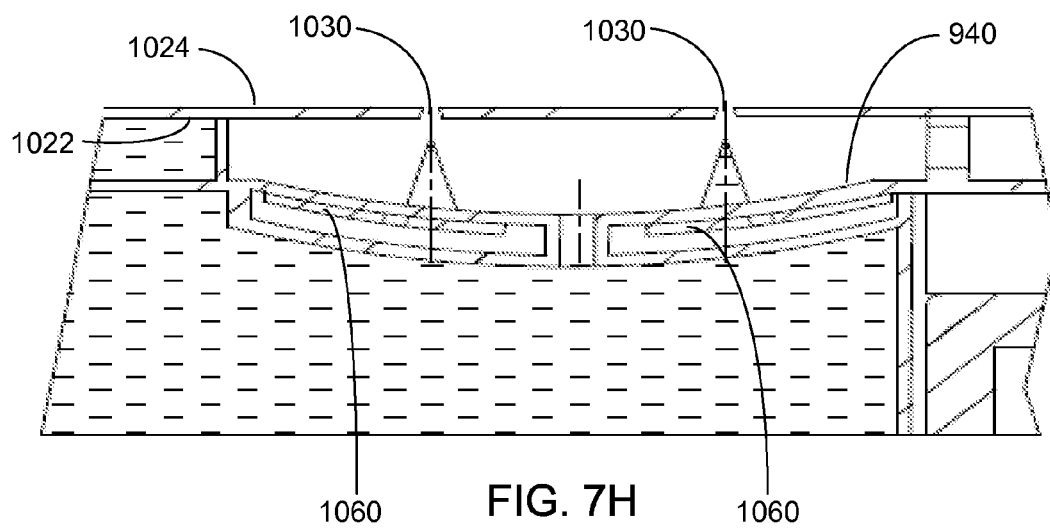
Figure 7I:
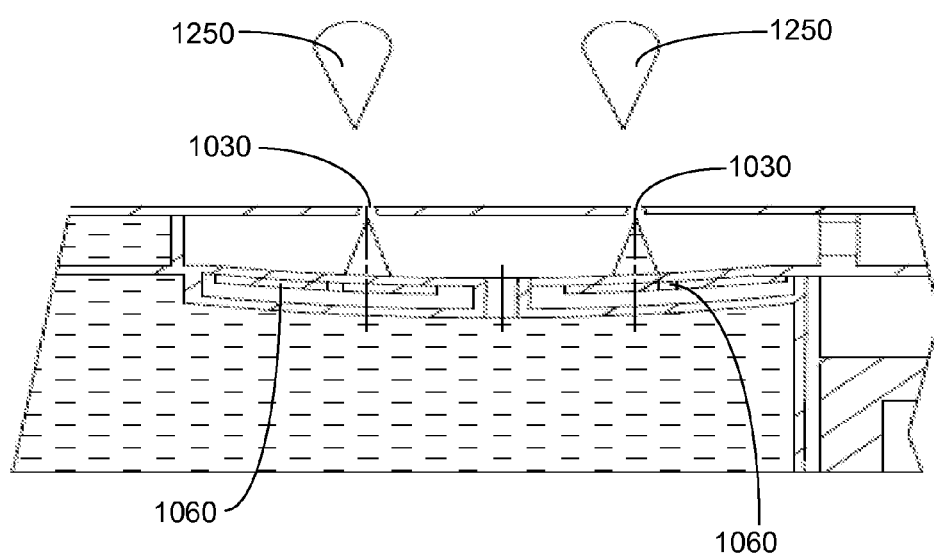
Figure 8:
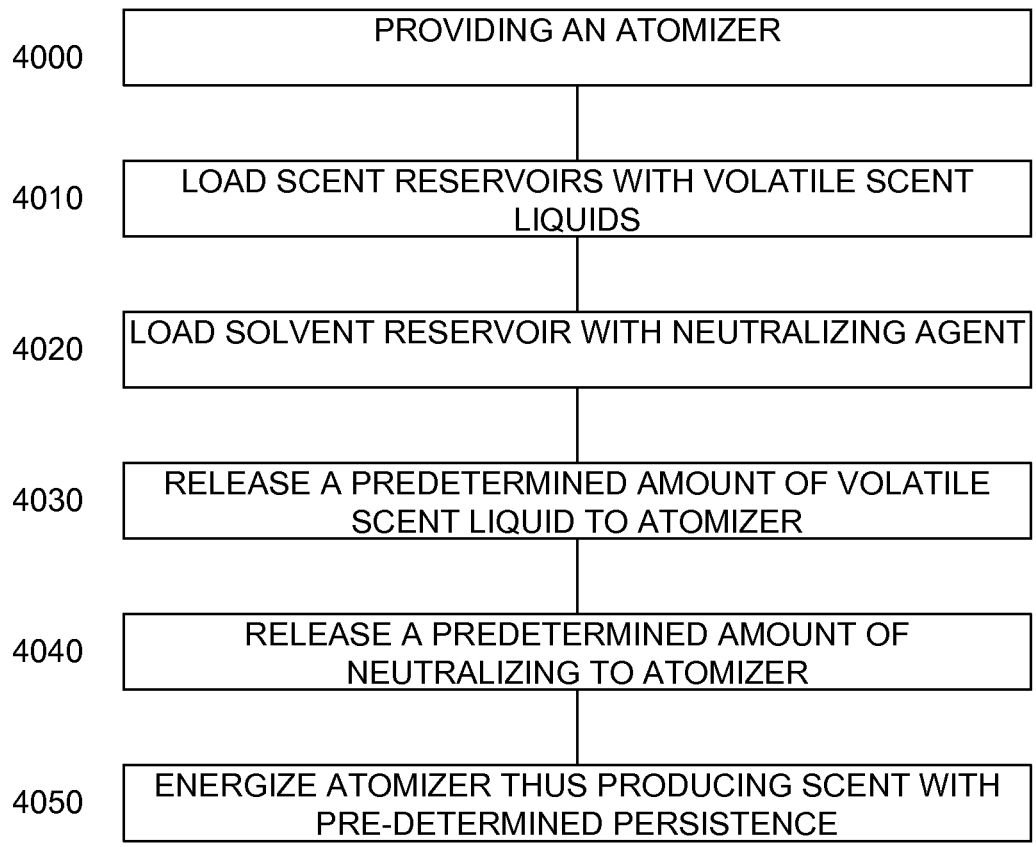
FIG. 8 illustrates a high level flow chart of an embodiment of a method of scent production utilizing a neutralizing agent to achieve a pre-determined persistence.
Figure 9A:
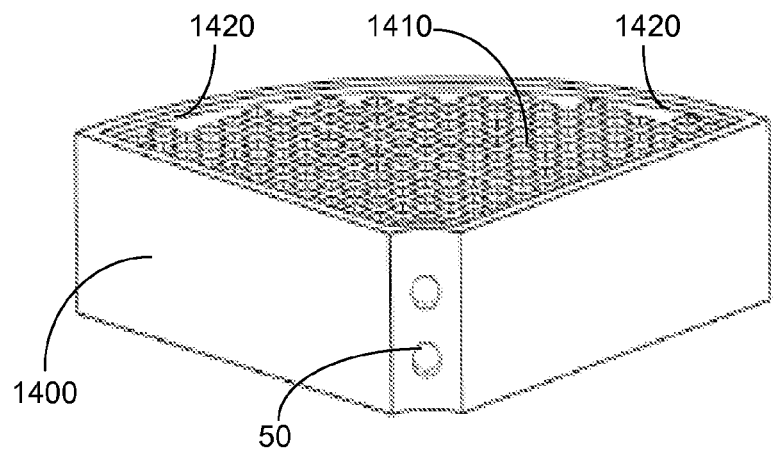
FIG. 9A illustrates a perspective view of a scent reservoir comprising scented material.
Figure 9B:
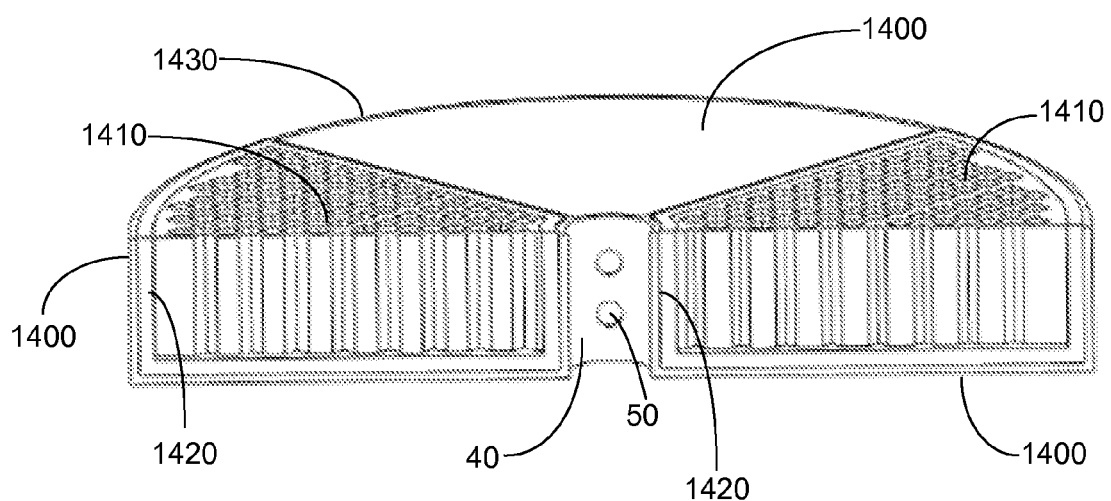
FIG. 9B illustrates a side cut view of a multi-scent cartridge comprising a plurality of the scent reservoirs of FIG. 9A.
Figure 10A:
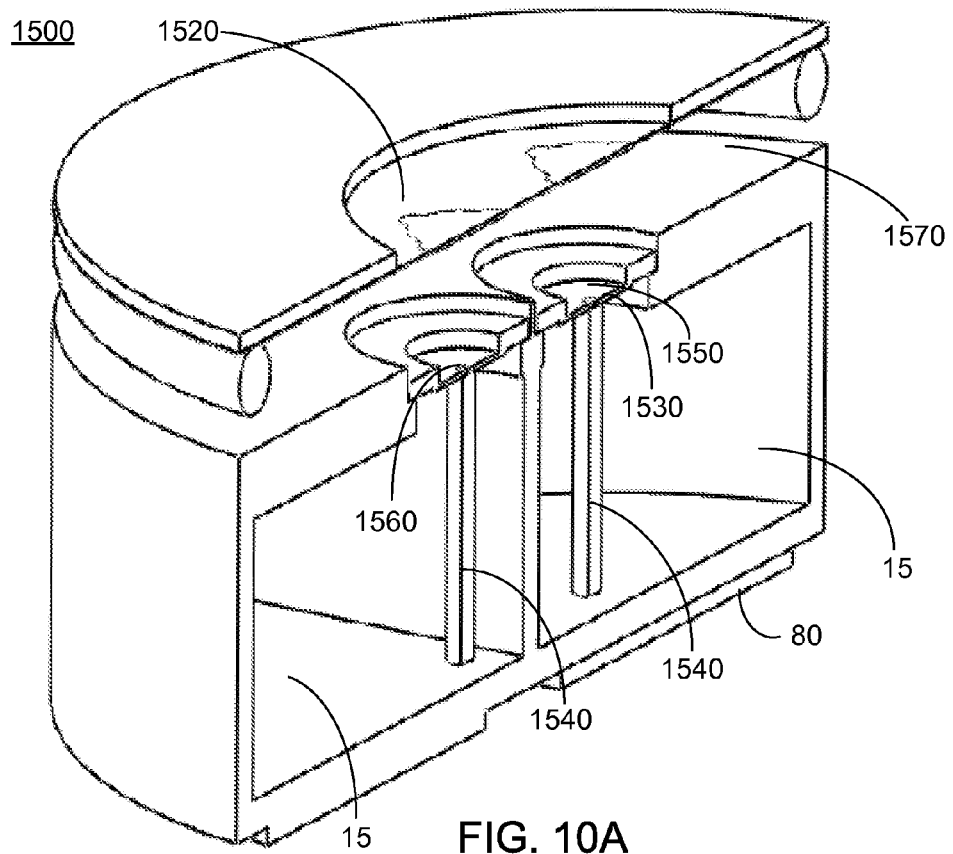
FIG. 10A illustrates a side cut view of a scent producing apparatus comprising controllable release mechanisms arranged to spray volatile scent liquid and common solvent into an atomizer.
Figure 10B:
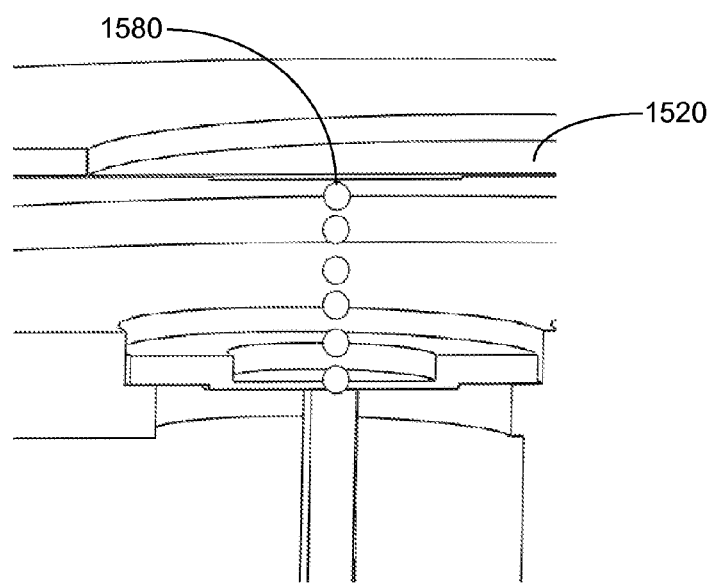
FIG. 10B illustrates a side cut view of various components of the scent producing apparatus of FIG. 10A.
Figure 10C:
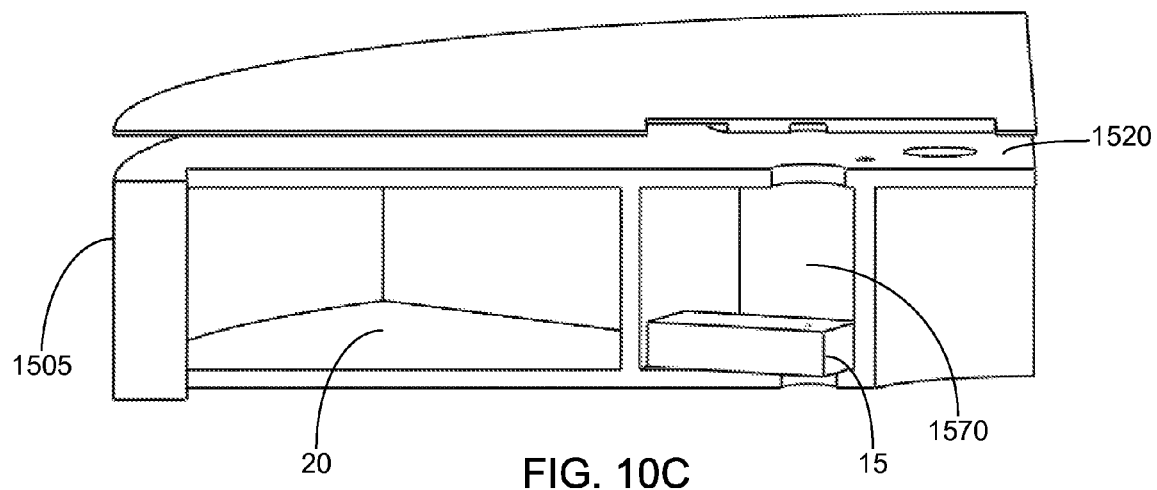
FIG. 10C illustrates a side cut view of a portion of the various components of FIG. 10B.

FIG. 7A illustrates a perspective view of various components of a scent producing apparatus 900, comprising a multi-scent cartridge 910 in communication with an atomizer 920; FIG. 7B illustrates a side cut view of scent producing apparatus 900; FIG. 7C illustrates a side cut view of multi-scent cartridge 910 in communication with atomizer 920 and exhibiting a plurality of controllable release mechanisms 930; FIG. 7D illustrates a side cut view of plurality of controllable release mechanisms 930 disposed on a common base 940, each controllable release mechanism 930 comprising a plurality of optional micro-needles 125; FIG. 7E illustrates a top view of the plurality of controllable release mechanisms 930 disposed on common base 940; FIG. 7F illustrates a top view of an atomizer plate 960; FIG. 7G illustrates a side cut view of a controllable release mechanism 930 with optional micro-needles 125 in a first position; FIG. 7H illustrates a side cut view of a controllable release mechanism 930 with optional micro-needles 125 in a second position; and FIG. 7I illustrates a side cut view of a controllable release mechanism 930 with optional micro-needles 125 in a third position, FIGS. 7A-7I being taken together.

In further detail, scent producing apparatus 900 comprises: multi-scent cartridge 910; atomizer 920; plurality of controllable release mechanisms 930; common base 940, exhibiting a first face 942 and a second face 944 opposing first face 942; a segmented nozzle device 960; a housing 970, forming a solvent reservoir 980; a housing extension 990, exhibiting a plurality of solvent exit ports 1000; and a pair of vibration isolation rings 1010. Atomizer 920 comprises: an atomizer plate 1020, exhibiting a first face 1022, a second face 1024 opposing first face 1022 and a plurality of release ports 1030 extending from first face 1022 to second face 1024, each release port 1030 forming the chassis section of a particular micro-valve; and a vibration mechanism 1040. In one embodiment, release ports 1030 are separated from each other by at least 300 microns. In one embodiment, vibration mechanism 1040 comprises a piezoelectric element. In one embodiment, vibration mechanism 1040 is disc shaped and exhibits a plurality of holes 1045 extending therethrough, each hole 1045 arranged to be aligned with the plurality of micro-valves associated with a particular controllable release mechanism 930. In another embodiment (not shown), vibration mechanism 1040 is ring shaped.

Each controllable release mechanism 930 comprises: a plurality of optional micro-needles 125 extending longitudinally from common base 940 to a tip end 127, each optional micro-needle 125 forming the needle section of a particular micro-valve, as will be described below; an input port 1050; a first translation mechanism 1060; a second translation mechanism 1070; a local scent reservoir border ring 1080, extending from common base 940 to atomizer plate 1020 and forming a local portion 1090 of the respective scent reservoir 20, as will be described further below; and a local solvent reservoir border ring 1100 extending from common base 940 to atomizer plate 1020 and forming with local scent reservoir border ring 1080 a local portion 1110 of solvent reservoir 980, as will be described further below. In one embodiment, the distance between common base 940 and atomizer plate 1020 is 100-300 microns. In one embodiment, first and second translation mechanisms 1060, 1070 are provided as a single translation mechanism, implemented in one particular embodiment as a piezo-electric element, without exceeding the scope. In one embodiment the diameter of each optional micro-needle 125 at common base 940 is 25-50 microns and in one further embodiment is about 30 microns.

Segmented nozzle device 960 comprises: a surface 1180, exhibiting a plurality of apertures 1190; and a nozzle extension 1200 comprising a plurality of nozzles 1210, each exhibiting an entry port 1220 and an exit port 1230, with each exit port 1230 constituted of a particular aperture 1190.

Common base 940 has disposed on first face 942 a plurality of controllable release mechanism 930, preferably radially displaced from each other. Common base 940 has further disposed on first face 942 a temporary solvent reservoir border ring 1120, extending from common base 940 to atomizer plate 1020 and forming a temporary solvent reservoir 1130 exhibiting a plurality of solvent entry ports 1140 extending through common base 940. Temporary solvent reservoir border ring 1120 exhibits a plurality of solvent passes 1150 therethrough, each arranged to provide communication between temporary solvent reservoir 1130 and each local portion 1110 of solvent reservoir 980 through the respective local solvent reservoir border ring 1100. In particular, at least one solvent pass 1150 is provided for each local portion 1110 of solvent reservoir 980. Each first translation mechanism 1060 is in communication with the respective local portion 1090 of scent reservoir 20 and particularly in communication with the area of second face 944 of common base 940 opposing the respective local portion 1090 of scent reservoir 20. Each second translation mechanism 1070 is in communication with the respective local portion 1110 of solvent reservoir 980 and particularly in communication with the area of second face 944 of common base 940 opposing the respective local portion 1110 of solvent reservoir 980.

Each of the plurality of optional micro-needles 125 is arranged to mate with a respective one of release ports 1030, thereby forming a micro-valve, the plurality of micro-valves forming a micro-valve array. Preferably, a portion of each optional micro-needle 125, and particularly the portion extending through release ports 1030 are conically shaped with an apex extending away from common base 940. Release ports 1030 are preferably similarly conically shaped, such that when the respective optional micro-needles 125 are in the first position, as will be described below, each of the respective optional micro-needles 125 is seated against the inner walls of the respective release port 1030. In one embodiment the respective optional micro-needles 125 are seated flush against the inner walls of the respective release port 1030 when in the first position. Preferably, each release port 1030 exhibits a diameter of about 30 microns at first face 1022 of atomizer plate 1020, matching the diameter of optional micro-needles 125 when completely seated therein.

Multi-scent cartridge 910 is in all respects similar to multi-scent cartridge 10, with the exception that solvent reservoirs 30 are not provided. Advantageously, this allows for the placement of a greater number of scent reservoirs 20 in multi-scent cartridge 910 than in multi-scent cartridge 10. Each scent reservoir 20 comprises volatile scent liquid 1160. Each controllable release mechanism 930 is associated with one of the plurality of scent reservoirs 20 and each input port 1050 extends through common base 940 into the respective scent reservoir 20. Preferably, each input port 1050 comprises a one-way valve, allowing for volatile scent liquid 1160 to flow only into the respective local portion 1090 of the respective scent reservoir 20.

Solvent reservoir 980 comprises common solvent 1170. The term common solvent is used herein as a solvent used for the contents of each of the scent reservoirs 20, and in one particular embodiment is water. Housing extension 990 extends through multi-scent cartridge 910 and is in communication with common base 940, with each of the plurality of solvent exit ports 1000 in communication with a respective one of the plurality of solvent entry ports 1140 and forming a pass for common solvent 1170 into temporary solvent reservoir 1130. Preferably, housing extension 990 comprises a one-way valve, allowing for common solvent 1170 to flow only into local solvent reservoir 1130. Vibration mechanism 1040 is in communication with second face 1024 of atomizer plate 1020. Vibration isolation rings 1010 are arranged to isolate housing 970 from multi-scent cartridge 910 such that when multi-scent cartridge 910 is vibrated, as will be described below, housing 970 is not vibrated. Entry port 1220 of each nozzle 1210 is in communication with second face 1024 of atomizer plate 1020 via a respective hole 1045 of vibration mechanism 1040. Specifically, entry port 1220 of each nozzle 1210 is in communication with the plurality of micro-valves associated with a particular controllable release mechanisms 930. In one embodiment, housing 970, multi-scent cartridge 910, atomizer 920 and nozzle extension 1200 are placed inside an outer housing 1240.

In one embodiment, housing 970 is removable and solvent reservoir 980 can be refilled when exhausted of common solvent 1170. In another embodiment, an opening (not shown) is provided in housing 970 to allow refilling of solvent reservoir 980 when exhausted of common solvent 1170. In one embodiment, multi-scent cartridge 910 is removable from scent producing apparatus 900 and can be replaced with a new multi-scent cartridge 910 when one or more scent reservoirs 20 are exhausted of volatile scent liquid 1160. In another embodiment, openings are provided to the plurality of scent reservoirs 20 (not shown) to allow refilling of any of the plurality of scent reservoirs 20 when exhausted of volatile scent liquid 1160.

As described above in relation to FIGS. 2A-2G, common solvent 1170 stored in solvent reservoir 980 is arranged to enter housing extension 990, aided by the force of gravity. In an alternative embodiment (not shown) a positive pressure mechanism is supplied. Common solvent 1170 thus enters temporary solvent reservoir 1130 and via solvent passes 1150 to each local portion 1110 of solvent reservoir 980. Volatile scent liquid 1160 from each scent reservoir 20 enters the respective local portion 1090 via the respective input port 1050. In one embodiment, the volatile scent liquid 1160 flows through input port 1050 aided by the force of gravity, as described above in relation to common solvent 1170. In another embodiment, volatile scent liquid 1160 flows through input port 1050 aided by capillary action.

In an embodiment where optional micro-needles 125 are not provided, the diameter of release ports 1030 are arranged to be small enough such that volatile scent liquid 1160 and common solvent 1170 stored in a controllable release mechanism 930 cannot exit through the respective release ports 1030 solely in response to gravity, the diameter of release ports 1030 being selected responsive to the viscosity of the volatile scent liquid 1160 and common solvent 1170.

In operation, each controllable release mechanism 930 is arranged to release a controlled amount of volatile scent liquid 1160 from a particular associated scent reservoir 20, and common solvent 1170 into atomizer 920, as described further below. In a first position, wherein first translation mechanism 1060 and second translation mechanism 1070 are each not contracted, in one embodiment each optional micro-needle 125 is seated against the walls of the respective release port 1030, thereby closing the respective release port 1030. In one embodiment each optional micro-needle 125 is seated flush against the walls of the respective release port 1030, thereby closing the respective release port 1030. In order to release a controlled quantity of volatile scent liquid 1160 and common solvent 1170 from a particular controllable release mechanism 930, a low frequency electrical signal and a DC electrical signal are provided by control circuitry 250 of FIG. 4 (not shown) to the associated first translation mechanism 1060 and second translation mechanism 1070. At a high state of the low frequency signal, first and second translation mechanisms 1060 and 1070 are contracted, thereby bending common base 940 and translating optional micro-needles 125 to a second position, wherein optional micro-needles 125 are removed from release ports 1030. In one embodiment, optional micro-needles 125, in the second position, are only partially removed from release ports 1030 so as to allow entry of volatile scent liquid 1160 or common solvent 1170 into the respective release ports 1030.

At a low state of the low frequency signal, first and second translation mechanisms 1060 and 1070 partially expand to translate optional micro-needles 125 to a third position, the third position being between the first position and the second position. First and second translation mechanisms 1060 and 1070 remain partially contracted because of the DC electrical signal. As optional micro-needles 125 are translated from the second position to the third position, droplets 1250 of volatile scent liquid 1160 and common solvent 1170 are released through the respective release port 1030 onto second face 1024 of atomizer plate 1020. Thus, droplets 1250 of volatile scent liquid 1160 and common solvent 1170 are released using Drop on Demand technology with the addition of optional micro-needles 125. Advantageously, in the first position optional micro-needles prevent volatile scent liquid 1160 and common solvent 1170 from being uncontrollably released through release ports 1030. Further advantageously, volatile scent liquid 1160 and common solvent 1170 are disposed onto second face 1024 of atomizer plate 1020 while being stored in communication with first face 1022 of atomizer plate 1020.

In the embodiment where optional micro-needles 125 are not provided, first and second translation mechanisms 1060 and 1070 are arranged to expand so as to release droplets 1250 of volatile scent liquid 1160 and common solvent 1170, as known to one skilled in the art of Drop on Demand technology. Specifically, when first and second translation mechanisms 1060 and 1070 expand, common base 940 bends thereby applying pressure to the volatile scent liquid 1160 and common solvent 1170. Responsive to the applied pressure, droplets 1250 of volatile scent liquid 1160 and common solvent 1170 are released through the respective release port 1030 onto second face 1024 of atomizer plate 1020.

Control circuitry 250 is further arranged to provide a high frequency electrical signal to vibration mechanism 1040 thereby vibrating atomizer plate 1020 and atomizing any droplets 1250 of volatile scent liquid 1160 and common solvent 1170 found on second face 1024 of atomizer plate 1020. In an exemplary embodiment the high frequency electrical signal exhibits a frequency range of 1-2 MHz, however this is not meant to be limiting in any way. The atomized droplets 1250 of volatile scent liquid 1160 and common solvent 1170 enter the associated nozzle 1210, via the entry port 1220, and travel through the nozzle 1210 and out through exit port 1230. The atomized droplets 1250 of volatile scent liquid 1160 and common solvent 1170 mix inside nozzle 1210, such that a scent is released external of segmented nozzle device 960. Advantageously, each of the various atomized droplets 1250 of volatile scent liquids 1160 in combination with common solvent 1170 meet externally of the respective exit port 1230, and are not mixed within scent producing apparatus 900. In particular, each of the scents from the respective scent reservoirs 20 are kept isolated from other scents by the operation of segmented nozzle device 960. Thus, production of a particular scent is not contaminated by other scents which may remain on the inner walls of segmented nozzle device 960.

Preferably, control circuitry 250 is arranged to provide the high frequency electrical signal to vibration mechanism 1040 during the release of droplets 1250 of volatile scent liquid 1160 and common solvent 1170. Advantageously, any liquid in the vicinity of release ports 1030 are atomized and do not interfere with the releasing of additional droplets 1250 of volatile scent liquid 1160 and common solvent 1170.

In one embodiment, the amount and size of optional micro-needles 125 in local portion 1090 of each scent reservoir 20 and each local portion 1110 of solvent reservoir 980 are chosen such that a predetermined quantity of common solvent 1170 is released for each released quantity of volatile scent liquid 1160. In one embodiment the quantity of released common solvent 1170 is about 20 times the quantity of released volatile scent liquid 1160. In one embodiment, the frequencies of the low frequency electrical signals provided to first translation mechanism 1060 and second translation mechanism 1070 are chosen such that a predetermined quantity of common solvent 1170 is released for each released quantity of volatile scent liquid 1160. In one embodiment, the high frequency electrical signal is provided to vibration mechanism 1040 at predetermined intervals and the lengths of time the low frequency electrical signals are provided to first translation mechanism 1060 and second translation mechanism 1070 are chosen such that a predetermined quantity of common solvent 1170 is released for each released quantity of volatile scent liquid 1160.

In order to cease the production of the scent, control circuitry 250 is arranged to disconnect electrical signals from vibration mechanism 1040, and in response atomizer plate 1020 ceases to vibrate. Control circuitry 250 is further arranged to disconnect electrical signals from the respective first and second translation mechanisms 1060 and 1070. In one embodiment, first and second translation mechanism 1060 and 1070 fully expand, thereby returning optional micro-needles 125 to the first position.

In order to produce a compound scent, control circuitry 250 applies a low frequency electric power to a plurality of first and second translation mechanisms 1060 and 1070, thereby releasing controlled quantities of different volatile scent liquids 1160 and common solvent 1170 through the respective release ports 1030, as described above. In one embodiment, each of the different volatile scent liquids 1160 produces a unique scent. A plurality of scents is then produced, as described above, each scent exiting a respective nozzle 1210. The plurality of scents mix as they exit the respective nozzles 1210, thereby creating a compound scent.

The above has been described in an embodiment wherein segmented nozzle device 960 is provided. Advantageously, each scent has a separate nozzle 1210 and therefore there is no requirement to clean atomizer plate 1020. In another embodiment, segmented nozzle device 960 is not provided. As described above in relation to FIGS. 3A-3G, after the production of a scent is completed atomizer plate 1020 is ultrasonically cleaned. As described above, in one embodiment, at the end of scent production, optional micro-needles 125 are returned to the first position so that no droplets 1250 are released to second face 1024 of atomizer plate 1020. A medium to high frequency electrical signal, in one non-limiting embodiment being from 40 kHz to 400 kHz, is supplied to vibration mechanism 1040, thus vibrating atomizer plate 1020. Any residual volatile scent liquid 1160 and common solvent 1170 on second face 1024 of atomizer plate 1020 is promptly atomized, or nebulized, and removed completely, thus ceasing scent production, and cleaning the previously issued scent from second face 1024 of atomizer plate 1020, allowing for production of a different subsequent scent without any residual scent from the previous scent production.

In another embodiment, multi-scent cartridge 910 is provided with one or more neutralizer reservoirs in place of one or more scent reservoirs 20. Each neutralizer reservoir is provided with a neutralizing agent. In one embodiment the neutralizing agent is an amphoteric substance arranged to neutralize any scent produced by scent producing apparatus 900 after a pre-determined time period. In one particular embodiment the neutralzing agent is a sodium bicarbonate solution. In another embodiment the neutralizing agent is a strongly basic liquid, preferably exhibiting a pH of greater than 9 to neutralize any acidic volatile scent liquid. In one further embodiment, common solvent 1170 in reservoir 980 is replaced with a neutralizing agent. In one further embodiment, an additional reservoir comprising a neutralizing agent is provided and is arranged to release the neutralizing agent in parallel with, or alternately with, common solvent 1170. During production of a scent, droplets 1250 of neutralizing agent are released onto second face 1024 of atomizer plate 1020 in addition to, or in place of, the common solvent, as described above. Thus, scent is produced by atomizer 920 with a pre-determined persistence. Advantageously, atomizer plate 1020 does not have to be ultrasonically cleaned, as no residual scent persists thereon. Further advantageously, the scent released by scent producing apparatus 900 does not persist in the vicinity of scent producing apparatus 900 for more than a pre-determined amount of time and a newly produced scent does not mix with previous scents.

FIG. 8 illustrates a high level flow chart of an embodiment of a method of scent production utilizing a neutralizing agent to achieve a pre-determined persistence. The method of FIG. 8 may be advantageously utilized with any of scent producing apparatus 200, 600 or 900, as described above. In stage 4000, an atomizer is provided, which in an exemplary embodiment may comprise any of the atomizers 240, 640 or 920 described above.

In stage 4010, each of the various scent reservoirs 20 are loaded with a particular volatile scent liquid. There is no requirement that each and every scent reservoir 20 be loaded with a unique volatile scent liquid, and a plurality of scent reservoirs 20 may be loaded with an identical volatile scent liquid without exceeding the scope.

In stage 4020, each of the one or more solvent reservoirs 30 are loaded with a neutralizing agent. In one embodiment each of solvent reservoirs 215, 980 respectively are loaded with the neutralizing agent. In one embodiment the neutralizing agent is an amphoteric substance arranged to neutralize any scent produced by the respective scent producing apparatus after a pre-determined time period. In one particular embodiment the neutralizing agent is a sodium bicarbonate solution. In another embodiment the neutralizing agent is a strongly basic liquid, preferably exhibiting a pH of greater than 9 to neutralize any acidic volatile scent liquid.

In stage 4030, a pre-determined quantity of one or more volatile scent liquids are released to the atomizer as described above, and in stage 4040 a pre-determined quantity of the neutralizing agent is further released to the atomizer. In stage 4050 the atomizer is energized thus atomizing the mix of volatile scent liquid and neutralizing agent to produce a scent with pre-determined persistence. The neutralizing agent preferably acts as a solvent for production of the scent, and equally acts to neutralize the scent after a pre-determined time period.

FIG. 9A illustrates a perspective view of a scent reservoir 1400. Scent reservoir 1400 is in all respects similar to solvent reservoir 30 of FIGS. 1A-1D, with the exception that scent reservoir 1400 comprises an inner mesh 1410. In one embodiment, inner mesh 1410 is impregnated with a scent. In another embodiment, inner mesh 1410 is coated with a scent. In one embodiment, inner mesh 1410 is composed of plastic. In one embodiment, the inner walls 1420 of scent reservoir 1400 are impregnated with a scent. In another embodiment, inner walls 1420 of scent reservoir 1400 are coated with a scent. In one embodiment, inner walls 1420 of scent reservoir 1400 are composed of plastic. Common solvent in scent reservoir 1400 absorbs scent from inner mesh 1410 and inner walls 1420.

FIG. 9B illustrates a side cut view of a multi-scent cartridge 1430. Multi-scent cartridge 1430 is in all respects similar to multi-scent cartridge 10 of FIGS. 1A-1J, with the exception that scent reservoirs 20 and solvent reservoirs 30 are replaced with scent reservoirs 1400 of FIG. 9A. Advantageously, no solvent reservoirs are needed in multi-scent cartridge 1430, thereby increasing the amount of different scents available in multi-scent cartridge 1430 and/or allowing for enlargement of scent reservoirs 1400. The operation of multi-scent cartridge 1430 is in all respects similar to the operation of multi-scent cartridge 10 and in the sake of brevity will not be further described.

In one embodiment, multi-scent cartridge 1430 replaces: multi-scent cartridge 10 in scent producing apparatus 200 of FIGS. 2A-2G and multi-scent cartridge 630 in scent producing apparatus 600 of FIGS. 3A-3G. In one embodiment, multi-scent cartridge 1430 replaces multi-scent cartridge 910 in scent producing apparatus 900 of FIGS. 7A-7I, whereby temporary solvent reservoir 1130 and local portions 1110 of solvent reservoir 980 are therefore not required.

FIG. 10A illustrates a side cut view of a scent producing apparatus 1500 comprising a multi-scent cartridge 1505 exhibiting a plurality of controllable release mechanisms 1510 each arranged to spray volatile scent liquid and common solvent into an atomizer 1520, FIG. 10B illustrates a side cut view of various components of scent producing apparatus 1500 and FIG. 10C illustrates a side cut view of a portion of the various components of FIG. 10A, the figures being described together. Multi-scent cartridge 1505 is in all respects similar to either multi-scent cartridge 10 of FIGS. 1A-1J or multi-scent cartridge 630 of FIGS. 3A-3G, with the exception that controllable release mechanisms 80 are replaced with controllable release mechanisms 1530, comprising: a capillary wick 1540; a spray mechanism 1550; and a spray nozzle 1560. The construction and operation of capillary wick 1540 is as described in U.S. Pat. No. 4,301,093 issued on Nov. 17, 1981 to Eck, the entire contents of which are incorporated herein by reference. Atomizer 1520 is in all respects similar to either atomizer 240 of FIGS. 2A-2G or atomizer 640 of FIGS. 3A-3G. The arrangement of scent producing apparatus 1500 is in all respects similar to the arrangement of either scent producing apparatus 200 of FIGS. 2A-2G or scent producing apparatus 600 of FIGS. 3A-3G, with the exception that atomizer 1510 is separated from multi-scent cartridge 1505 by an air gap 1570. In one embodiment, air gap 1570 is about 0.5 mm, measured from the multi-scent cartridge to the atomizer. As described above in relation to controllable release mechanisms 80, a controllable release mechanism 1530 is provided for each scent reservoir 20 and solvent reservoir 30, or scent drop on demand unit 15 and solvent drop on demand unit as illustrated in FIG. 10C. Each spray nozzle 1560 is in communication with a respective port 70 of multi-scent cartridge 1505, the associated capillary wick 1540 extending into the respective scent reservoir 20, solvent reservoir 30, scent drop on demand unit 15, or solvent drop on demand unit. Each spray mechanism 1550 is connected to the associated capillary wick 1540.

In operation, volatile scent liquid and common solvent are released from the respective scent reservoirs 20 and solvent reservoirs 30, or scent drop on demand units 15 and solvent drop on demand units, by controllable release mechanism 1530, preferably responsive to a control circuitry (not shown). Particularly, spray mechanism 1550 is arranged to spray droplets 1580 of the respective volatile scent liquid or common solvent through spray nozzle 1560 towards an atomizer, the atomizer being one of atomizer 240 of FIG. 2C or atomizer 640 of FIG. 3D, preferably through a respective capillary channel 360 (not shown) as described above. In one embodiment, volatile scent liquid and common solvent are arranged to enter the respective capillary wick 1540 responsive to capillary action and in another embodiment spray mechanism 1550 is arranged to pull volatile scent liquid or common solvent into the respective capillary wick 1540. The sprayed droplets 1580 enter the atomizer and are then atomized, as described above in relation to scent producing apparatus 200 of FIGS. 2A-2G and scent producing apparatus 600 of FIGS. 3A-3G.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:

1. A scent producing apparatus, the apparatus comprising:
a single atomizer;
a control circuitry; and
a plurality of scent reservoirs each with a respective controllable release mechanism, said respective controllable release mechanism arranged to release a controlled quantity of the contents of said scent reservoir to said single atomizer responsive to said control circuitry,
at least one solvent reservoir with a respective controllable release mechanism, each of said respective solvent reservoir controllable release mechanism arranged to release a controlled quantity of the contents of said at least one solvent reservoir to said single atomizer responsive to said control circuitry,
wherein the contents of each of said plurality of scent reservoirs comprise scent liquid and the contents of said at least one solvent reservoir consists essentially of water, and
wherein said single atomizer is arranged, responsive to said control circuitry, to vibrate at a predetermined frequency, said vibration arranged to atomize said released controlled quantity of contents of said plurality of scent reservoirs.

2. The scent producing apparatus according to claim 1, wherein the plurality of scent reservoirs are radially arrayed about a common center axis comprising an extension of the at least one solvent reservoir.

3. The scent producing apparatus according to claim 1, wherein each of said scent reservoirs comprises a port towards said single atomizer and each of the respective scent reservoir controllable release mechanisms comprises a piezoelectric element in communication with said port, said piezoelectric element coupled to an output of said control circuitry and responsive to a first signal state at said output of said control circuitry to release a predetermined quantity of the contents of said scent reservoir through said port to said single atomizer, and to a second signal state to cease the release of the controlled quantity of the contents of said scent reservoir through said port to said single atomizer.

4. The scent producing apparatus according to claim 3, wherein said first signal state exhibits a plurality of sub-states, each of said plurality of sub-states arranged to enable said piezoelectric element of the respective scent reservoir controllable release mechanism to release through said port a different predetermined quantity of the contents of said scent reservoir.

5. The scent producing apparatus according to claim 1, further comprising at least one solvent reservoir with a respective controllable release mechanism, said solvent reservoir controllable release mechanism arranged to release a controlled quantity of the contents of said at least one solvent reservoir to said single atomizer responsive to said control circuitry,
wherein said at least one solvent reservoir comprises a port towards said single atomizer and wherein said respective solvent reservoir controllable release mechanism comprises a piezoelectric element in communication with said port, said piezoelectric element of said respective solvent reservoir controllable release mechanism coupled to an output of said control circuitry and responsive to a first signal state at said output of said control circuitry to release a predetermined quantity of the contents of said at least one solvent reservoir through said port to said single atomizer, and to a second signal state to cease the release of the controlled quantity of the contents of said at least one solvent reservoir through said port to said single atomizer.

6. The scent producing apparatus according to claim 5, wherein said first signal state exhibits a plurality of sub-states, each of said plurality of sub-states arranged to enable said piezoelectric element of said solvent reservoir to release through said port a different predetermined quantity of the contents of said solvent reservoir.

7. The scent producing apparatus according to claim 1, wherein said single atomizer comprises a plurality of segments, each of said scent reservoirs associated with, and arranged to release the controlled quantity to a particular one of said plurality of segments.

8. The scent producing apparatus according to claim 7, wherein said control circuitry is arranged to enable each of at least two of said plurality of scent release mechanisms to release a controlled quantity of the contents of the respective scent reservoir to the respective atomizer segment so as to produce a compound scent.

9. The scent producing apparatus according to claim 7, further comprising a plurality of solvent reservoirs each with a respective controllable release mechanism arranged to release a controlled quantity of the contents of the respective solvent reservoir to a respective one of the plurality of segments of said single atomizer responsive to said control circuitry,
wherein said control circuitry is arranged to enable at least two of said scent reservoir controllable release mechanisms and at least two of said solvent reservoir controllable release mechanisms to release a controlled quantity of the contents of the respective scent reservoirs and solvent reservoirs to said single atomizer so as to produce a compound scent.

10. The scent producing apparatus according to claim 1, wherein said single atomizer comprises:
a plate exhibiting a plurality of perforations extending from a first face of said plate to a second face of said plate opposing said first face;
a plurality of micro-needles in communication with said plate, each of said plurality of micro-needles extending longitudinally from a base end to a tip end, and arranged to mate with one of said plurality of perforations; and
at least one of:
a translation mechanism in communication with one of said plate and said plurality of micro-needles and responsive to said control circuitry, said translation mechanism arranged to translate said plurality of micro-needles in relation to said plate from a first position wherein each of said plurality of micro-needles is seated within a respective one of said plurality of said perforations to a second position wherein each of said plurality of micro-needles is at least partially removed from a wall of said respective one of said plurality of perforations; and
a vibrator in communication with at least one of said plate and said plurality of micro-needles.

11. The scent producing apparatus according to claim 1, wherein said single atomizer comprises a plate exhibiting a plurality of release ports extending from a first face of said plate to a second face of said plate opposing said first face and a vibrator in communication with the plate and responsive to said control circuitry, and wherein each of said plurality of controllable release mechanisms comprises:

a local portion of a respective one of said plurality of scent reservoirs;

a micro-needle, in communication with said plate of said atomizer and extending longitudinally from a base end to a tip end, said micro-needle arranged to mate with one of said plurality of release ports; and a translation mechanism in communication with said micro-needle and responsive to said control circuitry, wherein said control circuitry is arranged to:

translate, via said translation mechanism, said micro-needle in relation to said plate from a first position, wherein said micro-needle is seated within the respective release port, to a second position wherein said micro-needle is at least partially removed from a wall of the respective release port; and vibrate the plate, said atomization of the released controlled quantity of the contents of the respective scent reservoir responsive to said vibration of said plate, wherein said release of the controlled quantity of the contents of the respective scent reservoir is responsive to said micro-needle being in said second position.

12. The scent producing apparatus according to claim 1, wherein each of said plurality of scent reservoirs comprises a scented material.

13. A method of scent production comprising:

providing a single atomizer;

providing a plurality of scent reservoirs, each arranged to comprise a volatile scent liquid;

providing at least one solvent reservoir comprising a common solvent for the super-concentrated volatile scent liquids, the common solvent consisting essentially of water; and releasing, responsive to a control circuitry, a controlled quantity of volatile scent liquid from at least one of said provided plurality of scent reservoirs to said provided single atomizer;

releasing a controlled quantity of common solvent from said provider at least one solvent reservoir to the provided atomizer, and vibrating, responsive to the control circuitry, said provided single atomizer at a predetermined frequency, said vibration arranged to atomize said released controlled quantity of contents of said plurality of scent reservoirs to thereby produce a scent, and wherein the volatile scent liquid of each of the plurality of scent reservoirs is a super concentrated volatile scent liquid.

14. The method of claim 13, wherein the provided single atomizer comprises a plurality of segments each associated with a particular one of the provided plurality of scent reservoirs, and wherein said releasing a controlled quantity of volatile scent liquid from at least one of said provided plurality of scent reservoirs to said provided single atomizer comprises releasing a controlled quantity of volatile scent liquid from at least one of said provided plurality of scent reservoirs to the associated segment of the provided single atomizer.

15. The method of claim 14, wherein said releasing a controlled quantity of volatile scent liquid from at least one of said provided plurality of scent reservoirs to said provided single atomizer comprises releasing a controlled quantity of volatile scent liquid from each of a plurality of said provided plurality of scent reservoirs to the associated atomizer segment of the provided single atomizer thereby producing a compound scent.

16. The method of claim 13, wherein said releasing a controlled quantity of volatile scent liquid from at least one of said provided plurality of scent reservoirs to said provided single atomizer comprises releasing a controlled quantity of volatile scent liquid from each of a plurality of said provided plurality of scent reservoirs to said provided single atomizer thereby producing a compound scent.

17. The method of claim 13, wherein said provided single atomizer comprises a plate and a plurality of micro-needles, and wherein the method further comprises, after producing the scent, ultrasonically cleaning a face of said plate and tip ends of said plurality of micro-needles.

18. The method of claim 13, wherein said provided single atomizer comprises a plate exhibiting a plurality of release ports extending from a first face of said plate to a second face of said plate opposing said first face, the method further comprising:

providing a plurality of controllable release mechanisms, each of said provided plurality of controllable release mechanisms in communication with one of said provided plurality of scent reservoirs and comprising a micro-needle, in communication with said plate of said provided single atomizer and extending longitudinally from a base end to a tip end, said micro-needle arranged to mate with one of said plurality of release ports; and translating said micro-needle of one of said plurality of controllable release mechanisms in relation to said plate from a first position, wherein said micro-needle is seated within the respective release port, to a second position wherein said micro-needle is at least partially removed from a wall of the respective release port, wherein said releasing a controlled quantity of volatile scent liquid is responsive to said micro-needle of the respective controllable release mechanism being in said second position.

19. The method of claim 13, wherein each of said plurality of scent reservoirs comprises a scented material.

20. The method of claim 13, further comprising:

releasing a pre-determined quantity of neutralizing agent to the atomizer; and atomizing, in the provided atomizer, the released pre-determined quantity of neutralizing agent together with the released predetermined quantity of volatile scent liquid to provide the scent.

\* \* \* \* \*